(12) United States Patent
Iwasaki et al.

(10) Patent No.: US 8,367,637 B2
(45) Date of Patent: *Feb. 5, 2013

(54) COMPOSITION FOR TREATING ARTHRITIC DISORDER

(75) Inventors: Norimasa Iwasaki, Hokkaido (JP); Akio Minami, Hokkaido (JP); Yasuhiko Kasahara, Hokkaido (JP); Tatsuya Igarashi, Hokkaido (JP); Daisuke Kawamura, Hokkaido (JP); Nobuo Ohzawa, Tokyo (JP); Mariko Imai, Tokyo (JP)

(73) Assignees: Mochida Pharmaceutical Co., Ltd., Tokyo (JP); National University Corporation Hokkaido University, Hokkaido (JP)

( * ) Notice: Subject to any disclaimer, the term of this patent is extended or adjusted under 35 U.S.C. 154(b) by 626 days.

This patent is subject to a terminal disclaimer.

(21) Appl. No.: 12/461,660

(22) Filed: Aug. 19, 2009

(65) Prior Publication Data

US 2010/0048506 A1 Feb. 25, 2010

Related U.S. Application Data

(60) Provisional application No. 61/090,043, filed on Aug. 19, 2008.

(51) Int. Cl.
*A61K 31/734* (2006.01)
*A61P 19/02* (2006.01)
*C08B 37/04* (2006.01)

(52) U.S. Cl. ............................................. 514/54; 536/3
(58) Field of Classification Search .................... 514/54; 536/3

See application file for complete search history.

(56) References Cited

U.S. PATENT DOCUMENTS

| 5,266,326 | A * | 11/1993 | Barry et al. ................... 424/423 |
| 6,451,772 | B1 | 9/2002 | Bousman et al. |
| 7,005,274 | B1 | 2/2006 | Terkeltaub et al. |
| 2005/0164980 | A1 | 7/2005 | Shimoboji |
| 2007/0021496 | A1 | 1/2007 | Terkeltaub et al. |

FOREIGN PATENT DOCUMENTS

| EP | 1 985 283 A1 | 10/2008 |
| JP | 7-504682 A | 5/1995 |
| JP | 2001-505809 A | 5/2001 |
| JP | 2001-517494 A | 10/2001 |
| JP | 2002-530440 A | 9/2002 |
| JP | 2003-520575 A | 7/2003 |
| WO | WO 94/00134 A1 | 1/1994 |
| WO | WO 98/25653 A2 | 6/1998 |
| WO | WO 99/15211 A1 | 4/1999 |
| WO | WO 01/20018 A2 | 3/2001 |
| WO | WO 03/087019 A1 | 10/2003 |
| WO | WO 2006/044342 A2 | 4/2006 |
| WO | WO 2007/083522 A1 | 7/2007 |

OTHER PUBLICATIONS

Firestein, G.S., Nature, May 15, 2003, 423, p. 356-361.*
Office Action issued on Feb. 2, 2010, in corresponding Japanese application No. 2009-500239 (3 pages), with English translation (3 pages).
Fragonas et al., "Articular cartilage repair in rabbits by using suspensions of allogenic chondrocytes in alginate," Biomaterials, 2000, 21:795-801.
Fukushima et al., The Merck Manual, 17th Edition, Japanese language edition, Nikkei Business Publications, Inc., 1999, 420-427, with English translation, 7 pages.
Igarashi et al., "Nankotsu Saise ni Muketa Kokasei Kojundo Tei-Endotoxin Alginic Acid Gel o Mochiita Shinki Ishoku System no Kaihatsu," J. Jpn. Orthop. Assoc., Aug. 25, 2007, 81(8):S838, with English translation, 3 pages.
Examination Report issued Dec. 10, 2010, in corresponding New Zealand application No. 584869, 2 pages.
Pelletier et al., "Amphiphilic derivatives of sodium alginate and hyaluronate for cartilage repair: Rheological properties," Journal of Biomedical Materials Research, 2000, 54(1):102-108.
International Search Report dated Nov. 18, 2008 in PCT/JP2008/065065, 4 pages.
International Preliminary Report on Patentability dated Jun. 9, 2009, in PCT/JP2008/065065, 17 pages.

* cited by examiner

*Primary Examiner* — Shaojia Anna Jiang
*Assistant Examiner* — Jonathan S Lau
(74) *Attorney, Agent, or Firm* — Foley & Lardner LLP

(57) ABSTRACT

The present invention provides compositions and methods for treating a joint disease containing as an active ingredient thereof a monovalent metal salt of alginic acid for which the endotoxin level thereof has been lowered to an extent that does not substantially induce inflammation or fever. As a result, it is possible to provide a composition for treating a joint disease which has the effects of protecting cartilage from mechanical irritation, inhibiting degenerative changes in cartilage caused by wear and inflammation, repairing cartilage injuries, suppressing inflammation and pain of joint tissue, inhibiting degeneration of synovial tissue, and inhibiting osteochondral destruction.

9 Claims, 21 Drawing Sheets

Fig. 1

| Edge Integration (new tissue relative to native cartilage) | Full | 2 |
|---|---|---|
| | Partial | 1 |
| | None | 0 |
| Smoothness of the cartilage surface | Smooth | 2 |
| | Intermediate | 1 |
| | Rough | 0 |
| Cartilage surface, degree of filling | Flush | 2 |
| | Slight depression | 1 |
| | Depressed/overgrown | 0 |
| Color of cartilage, opacity or translucency of the neocartilage | Transparent | 2 |
| | Translucent | 1 |
| | Opaque | 0 |

Fig. 2

| Characteristic | | Score |
|---|---|---|
| I. Nature of predominant tissue | Hyaline cartilage | 4 |
| | Mostly hyaline cartilage | 3 |
| | Mixed hyaline and fibrocartilage | 2 |
| | Mostly fibrocartilage | 1 |
| | Some fibrocartilage, mostly nonchondrocytic cells | 0 |
| II. Structural characteristics | | |
| A. Surface regularity | Smooth and intact | 3 |
| | Superficial horizontal lamination | 2 |
| | Fissures | 1 |
| | Severe disruption, including fibrillation | 0 |
| B. Structural integrity, homogeneity | Normal | 2 |
| | Slight disruption, including cysts | 1 |
| | Severe disintegration, disruptions | 0 |
| C. Thickness | 100% of normal adjacent cartilage | 2 |
| | 50-100% of normal cartilage | 1 |
| | 0-50% of normal cartilage | 0 |
| D. Bonding to adjacent cartilage | Bonded at both ends or graft | 2 |
| | Bonded at one end or partially at both ends | 1 |
| | Not bonded | 0 |
| III. Freedom from cellular changes of degeneration | | |
| A. Hypocellularity | Normal cellularity | 2 |
| | Slight hypocellularity | 1 |
| | Moderate hypocellularity or hypercellularity | 0 |
| B. Chondrocyte clustering | No clusters | 2 |
| | <25% of the cells | 1 |
| | 25-100% of the cells | 0 |
| IV. Freedom from degenerative changes in adjacent cartilage | | |
| | Normal cellularity, no clusters, normal staining | 3 |
| | Normal cellularity, mild clusters, moderate staining | 2 |
| | Mild or moderate hypo/hypercellularity, slight staining | 1 |
| | Severe hypocellularity, poor or no staining | 0 |
| V. Subcondral bone | | |
| A. Reconstruction of subchondral bone | Normal | 3 |
| | Reduced subchondral bone reconstruction | 2 |
| | Minimal subchondral bone reconstruction | 1 |
| | No subchondral bone reconstruction | 0 |
| B. Inflammatory response in subchondral bone region | | |
| | None/mild | 2 |
| | Moderate | 1 |
| | Severe | 0 |
| VI. Safranin-O staining | Normal or near normal | 3 |
| | Moderate | 2 |
| | Slight | 1 |
| | None | 0 |
| Total maximum score: | Sections with safranin-O | 28 |
| | Section with H&E | 25 |

Fig. 3
(A)
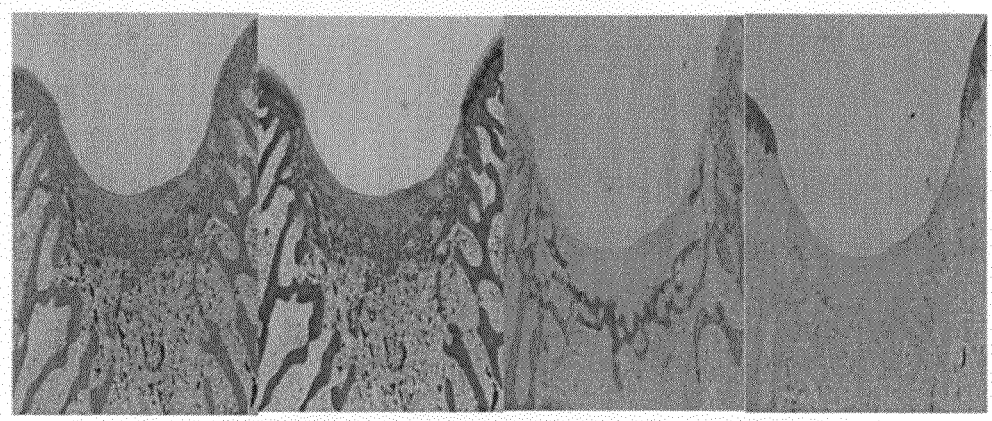
(B)
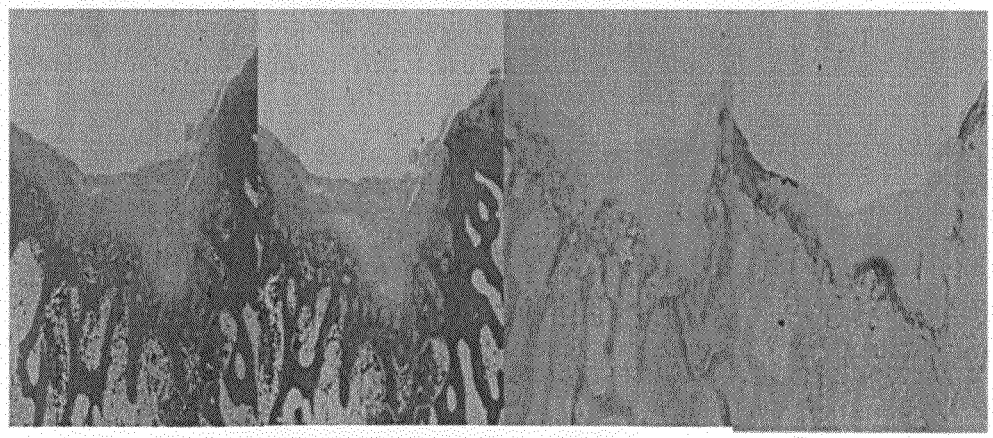

Fig. 4
(A)
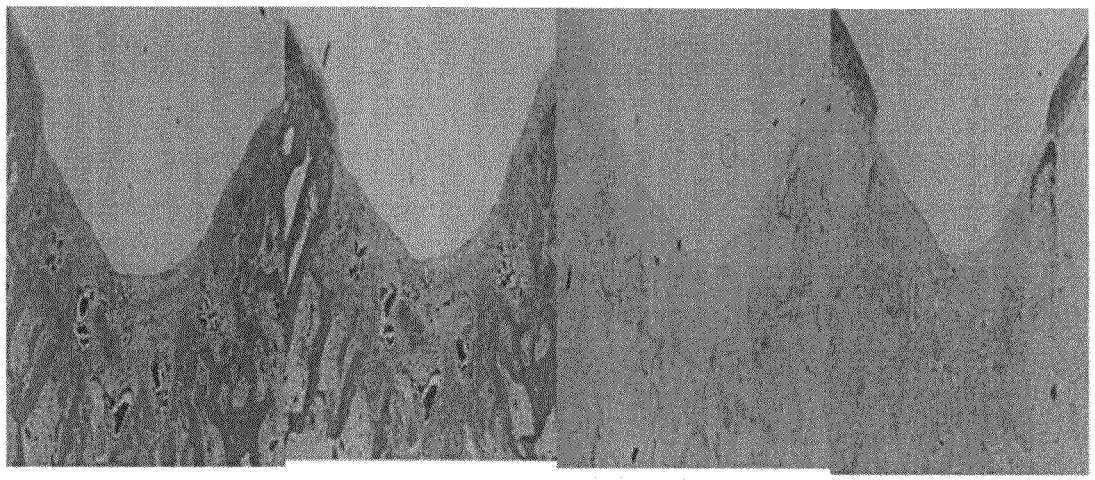
(B)
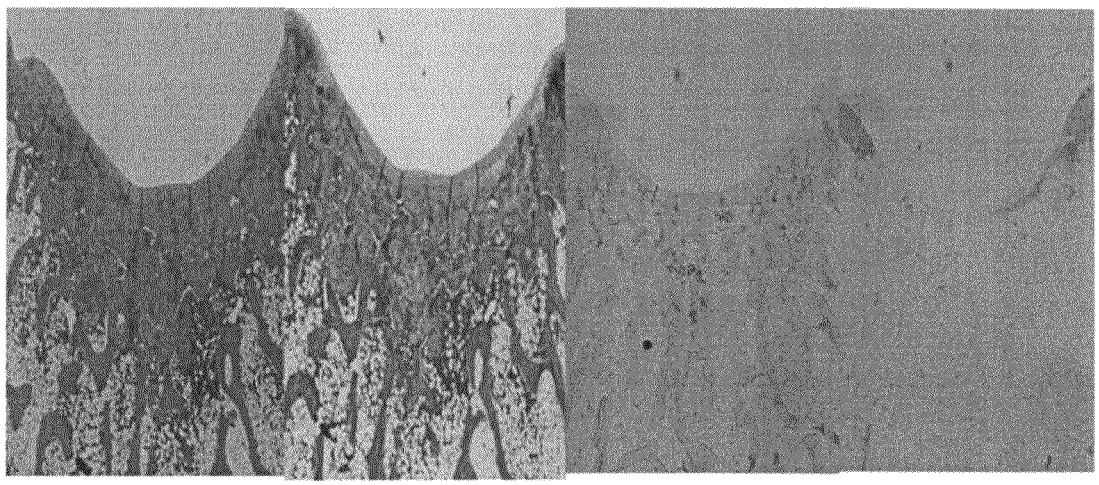

Fig. 5
(A)
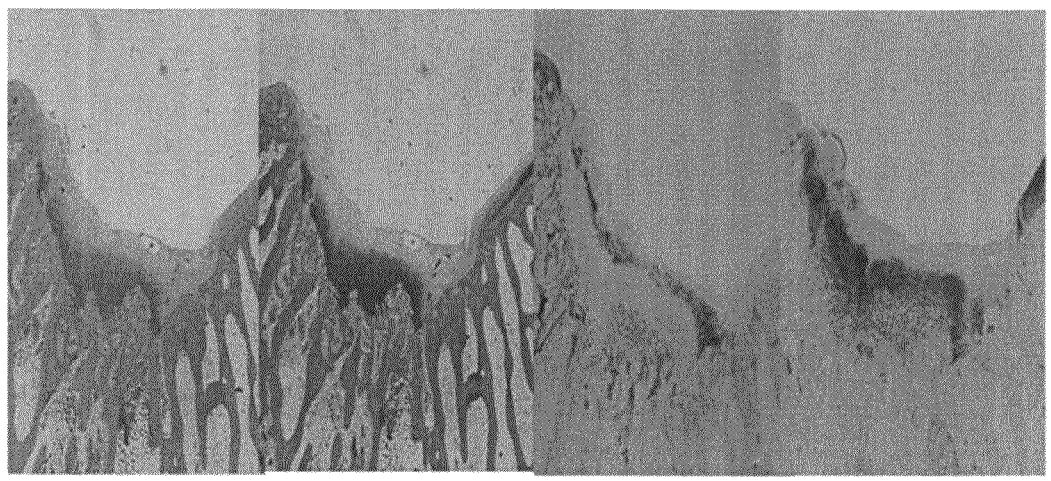
(B)
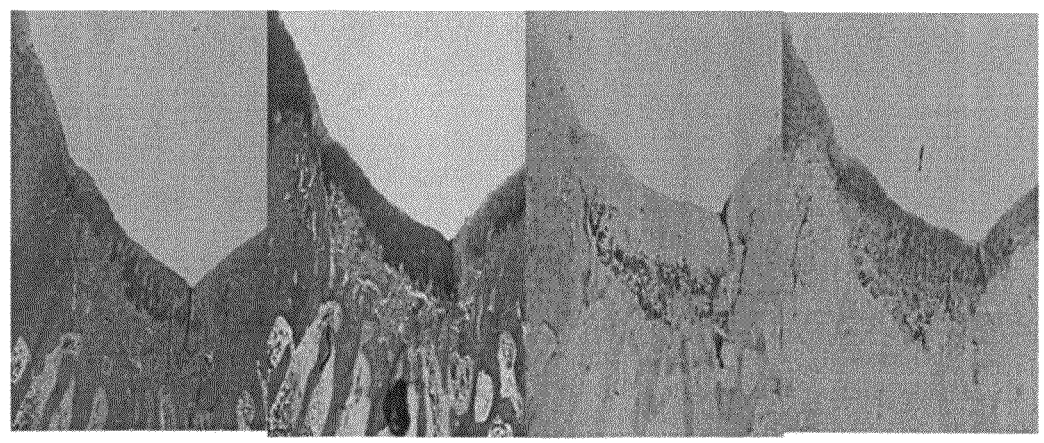

Fig. 6
(A)
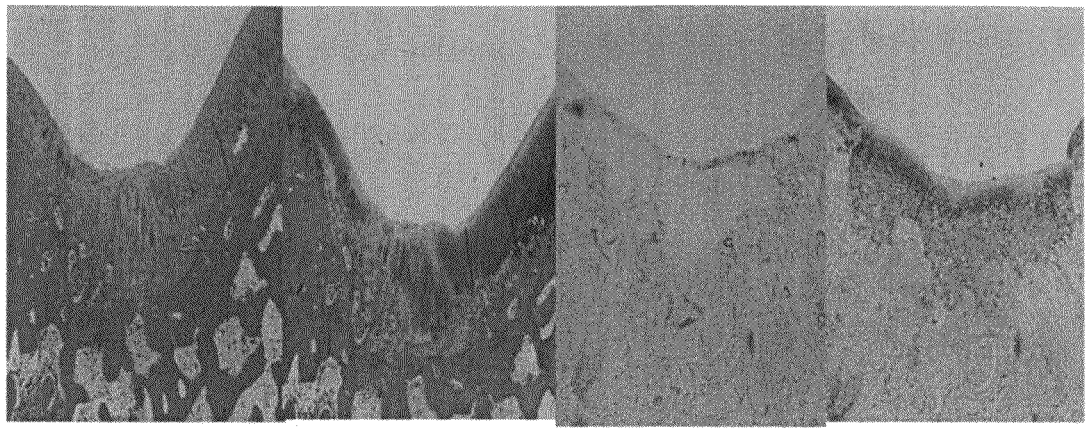
(B)
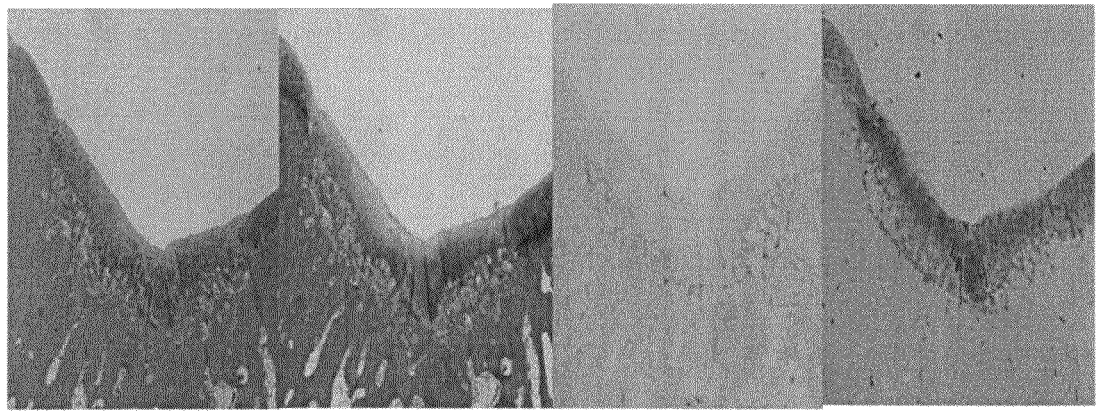

Fig. 7

| | | 4w | | | | | 12w | | |
|---|---|---|---|---|---|---|---|---|---|
| | Control (empty) | food grade alginate (no cell) | food grade alginate +Cells | pure alginate (no cell) | pure alginate +Cells | Control (empty) | food grade alginate (no cell) | food grade alginate +Cells | pure alginate (no cell) | pure alginate +Cells |
| Macro | | | | | | | | | | |
| Edge Integration | 0.80 | 0.50 | 0.50 | 0.63 | 0.90 | 0.71 | 0.50 | 1.00 | 1.00 | 1.57 |
| Smoothness of the cartilage surface | 0.20 | 0.25 | 0.50 | 0.75 | 1.20 | 0.43 | 0.75 | 0.75 | 1.00 | 1.43 |
| Cartilage surface, degree of filling | 0.20 | 0.75 | 0.50 | 1.13 | 1.40 | 0.57 | 1.00 | 1.00 | 1.71 | 1.71 |
| Color of cartilage | 0.20 | 0.00 | 0.17 | 0.63 | 0.70 | 0.14 | 0.25 | 0.25 | 0.86 | 1.00 |
| total | 1.40 | 1.50 | 1.67 | 3.13 | 4.20 | 1.86 | 2.50 | 3.00 | 4.57 | 5.71 |
| Histological | | | | | | | | | | |
| Nature of predominant tissue | 0.40 | 0.75 | 0.50 | 0.75 | 1.50 | 0.14 | 0.75 | 0.50 | 1.57 | 1.29 |
| surface regularity | 0.00 | 0.25 | 0.33 | 1.00 | 1.50 | 0.29 | 0.50 | 0.75 | 1.14 | 2.00 |
| Structural integrity, homogeneity | 0.80 | 1.00 | 0.67 | 0.50 | 0.90 | 0.43 | 0.75 | 0.75 | 1.00 | 1.00 |
| Thickness | 0.60 | 1.00 | 1.17 | 1.00 | 1.70 | 0.57 | 1.00 | 1.25 | 1.57 | 1.86 |
| Bonding to adjacent cartilage | 0.80 | 0.25 | 0.67 | 1.00 | 1.30 | 0.71 | 0.50 | 1.25 | 1.43 | 1.71 |
| Hypocellularity | 0.00 | 0.25 | 0.33 | 0.38 | 0.80 | 0.00 | 0.50 | 0.25 | 0.57 | 0.43 |
| Chondrocyte clustering | 0.00 | 0.50 | 0.50 | 0.25 | 0.20 | 0.00 | 0.50 | 0.25 | 0.29 | 0.43 |
| degenerative changes in adjacent cartilag | 1.20 | 0.75 | 1.50 | 1.88 | 2.80 | 1.29 | 0.75 | 2.00 | 2.57 | 2.86 |
| Reconstruction of subchondral bone | 0.80 | 0.50 | 1.17 | 1.00 | 1.30 | 1.14 | 1.00 | 2.25 | 1.71 | 2.14 |
| Inflammatory response | 1.40 | 1.25 | 1.00 | 1.63 | 1.70 | 1.71 | 0.75 | 1.50 | 1.86 | 2.00 |
| Safranin-O staining | 0.40 | 1.00 | 1.00 | 0.75 | 1.30 | 0.29 | 0.75 | 1.00 | 1.29 | 1.00 |
| total | 6.40 | 7.50 | 8.83 | 10.13 | 15.00 | 6.57 | 7.75 | 11.75 | 15.00 | 17.00 |
| total score | 7.80 | 9.00 | 10.50 | 13.25 | 19.20 | 8.43 | 10.25 | 14.75 | 19.57 | 22.71 |

COMPOSITION FOR TREATING ARTHRITIC DISORDER

CROSS-REFERENCE TO RELATED APPLICATIONS

This application claims priority to U.S. Provisional Application No. 61/090,043, filed Aug. 19, 2008, the entire contents of which are incorporated herein by reference.

TECHNICAL FIELD

The present invention relates to compositions and methods for treating a joint disease, including veterinary applications.

BACKGROUND

For example, articular cartilage is hyaline cartilage that is composed of a small number of cells, collagenous extracellular matrix, abundant proteoglycans and water. In the case of bone, since vascular and neural networks are present and bone has the ability to self-repair, even if a fracture has occurred, the fracture is frequently completely repaired. However, articular cartilage lacks vascular and neural networks. Consequently, it has virtually no potential for self-repair, and in the case of the formation of large cartilage defects in particular, the cartilage defect is not adequately repaired. Even at those portions that are repaired, fibrous cartilage is formed that has different mechanical properties than hyaline cartilage. Consequently, when a cartilage defect is formed, joint pain and loss of function are brought about that frequently progress to osteoarthritis. In addition, a cartilage defect can reach over a broad range as a result of symptoms progressing from the initial stages of osteoarthritis that began with wear of the surface of articular cartilage due to aging or excessive joint usage.

Although osteoarthritis (OA) is a degenerative disease in which articular cartilage is worn down due to aging and excessive joint use, in addition to the mechanical cause of wear, local inflammatory responses, such as the production of inflammatory cytokines by synovial cells and chondrocytes and the induction of algesic substances and proteases by inflammatory cytokines, are also said to be involved in joint destruction. Namely, accompanying wear of articular cartilage (mechanical damage), an inflammatory response is induced within joint tissue, self-destructive cartilage damage progresses due to this inflammatory response and mechanical damage further progresses due to decreased joint function, thereby resulting in a vicious cycle that further exacerbates the disease. Treatment of osteoarthritis focuses primarily on the removal of pain and inflammation at the affected area, and is commonly treated overseas with administration of non-steroid anti-inflammatory drugs. However, since renal function may be depressed in elderly patients, continuous oral administration of non-steroid anti-inflammatory drugs may be difficult from the viewpoint of safety. Products incorporating hyaluronic acid, which is a component of cartilage synovial fluid, improve the lubricating function of joints by being administered into a joint, and since these products also having analgesic action, they are widely used as joint function improving agents for osteoarthritis. However, in severe cases of osteoarthritis associated with advanced degeneration of cartilage and surrounding tissue, there is ultimately no other choice but to replace the joint with an artificial joint, thus making this one of the diseases for which there is a need to develop a novel therapeutic drug that inhibits and ultimately improves the advance of tissue degeneration (Reference 1).

Although the mechanism of occurrence of rheumatoid arthritis (RA) is not fully understood, it has been reported to involve inflammation and abnormal growth of the synovial membrane and an excessive immune response mediated by activated T-cells, resulting in progressive destruction of joint tissue. Although RA demonstrates symptoms resembling OA with respect to being associated with degeneration of joint tissue, RA is a type of autoimmune disease, and has a different pathology from that of OA. Recently, biological preparations have come to be used as RA therapeutic drugs targeted at an inflammatory cytokine in the form of TNF-α. These preparations have as active ingredients thereof anti-TNF-α antibodies or TNF receptors, and are thought to contribute to prevention of joint destruction by inhibiting the function of TNF-α. On the other hand, since these preparations inhibit the function of TNF-α systemically, serious adverse effects, including infectious diseases such as pneumonia and tuberculosis, present problems clinically. Thus, there is a need for a novel therapeutic drug that is highly safe and capable of inhibiting the progression of joint tissue degeneration.

Alginic acid is high molecular weight polysaccharide present in large amounts in brown algae that is a polymer obtained by linearly polymerizing two types of uronic acids in the form of D-mannuronic acid (M) and L-gluronic acid (G). In addition to exhibiting viscosity when in solution, since alginic acid also has the property of gelling in the presence of a cation having a valence of 2 or more, it is widely used as a thickener or gelling agent in foods, cosmetics and base materials of pharmaceutical preparations. A technology has come to be used that utilizes this gelling property of alginic acid by which beads embedded with cells are produced by dropping an alginic acid solution with cells suspended therein into a calcium ion solution. Attempts have been made to embed chondrocytes and the like in such beads followed by transplanting to a cartilage injury lesions. Reference 2 provides a discussion indicating that alginic acid can be used as a carrier without having any disadvantageous affects whatsoever on the cartilage injury lesions, and that alginic acid per se does not have any therapeutic effects. In addition, Reference 3 discloses that, although normal cartilage tissue was formed in a graft following the suspension of chondrocytes in a sodium alginate solution, injecting into a rabbit cartilage defect and curing the surface with $CaCl_2$ solution, fibrous cartilage is formed in the case of applying only alginic acid to the cartilage defect without containing cells therein. Reference 4 discloses a curable, self-gelling alginic acid composition, comprising a mixture of a soluble alginic acid salt and an insoluble alginic acid salt/gel, which contains chondrocytes and is injected into a cartilage defect.

In this manner, alginic acid is known to be a biopolymer capable of being used as a carrier of chondrocytes and the like, and has been attempted to be used as a transplant carrier that is injected into a cartilage defect together with cells and then cured by taking advantage of its gelling ability. However, the therapeutic effects of an alginic acid composition not containing cells are unknown, and the application of a non-curing alginic acid composition to joint disease has yet to be attempted.

[References]
1. Harumoto Yamada et al., "Drug therapy for osteoarthritis", Clin. Rheumatol., Vol. 18, 2006: pp. 298-306
2. Cay M. Mierisch et al., "Transforming Growth Factor-β in Calcium Alginate Beads for the Treatment of Articular Cartilage Defects in the Rabbit", The Journal of Arthroscopic and Related Surgery, Vol. 18, No. 8 (October), 2002: pp. 892-900

3. E. Fragonas et al., "Articular Cartilage Repair in Rabbits by Using Suspensions of Allogenic Chondrocytes in Alginate", Biomaterials, Vol. 21, 2000: pp. 795-801
4. International Publication WO 2006/044342

SUMMARY

Therapeutic drugs for osteoarthritis are required to provide comprehensive effects, including effects that protect cartilage from wear, effects that inhibit degenerative changes in cartilage caused by wear and inflammation, effects that repair cartilage injury lesion, and effects that suppress inflammation and pain. If a drug capable of inhibiting inflammation and suppressing pain in joints was able to be obtained, it could be applied to the treatment of frozen shoulder and suppression of joint pain in chronic rheumatoid arthritis.

Therapeutic drugs for rheumatoid arthritis are required to have therapeutic effects such as inhibiting abnormal proliferation of synovial cells and inhibiting destruction of osteochondral tissue accompanying an excessive immune response while also being highly safe with few adverse effects. Since RA is an autoimmune disease, it is difficult to avoid immunosuppressive adverse effects when attempting to obtain therapeutic effects. Although hyaluronic acid preparations are known to have a comparatively high degree of safety among pharmaceuticals able to be used for RA, intra-articular injection of hyaluronic acid is used for the purpose of suppressing pain in RA, and is not considered to be an RA therapeutic agent. Namely, the issue is to provide a novel drug capable of realizing both therapeutic effects for RA and a high degree of safety.

The inventors of the present invention conducted extensive studies to solve the above-mentioned problems. It was found that by intra-articularly injecting a composition containing a monovalent metal salt of alginic acid in which the endotoxin level had been lowered to a degree so as to substantially not cause inflammation or fever, cartilage degenerative changes are inhibited and effects are obtained that protect the cartilage in an experimental osteoarthritis model. In addition, it was found that this composition has the effect of suppressing pain in an experimental arthritis pain model. Moreover, it was also found that this composition has the effect of inhibiting destruction and degeneration of osteochondral tissue and inhibiting degeneration of synovial tissue in an experimental rheumatoid arthritis model, thereby leading to completion of the present invention.

This is the first instance in which a substance other than hyaluronic acid, which is a major component of synovial fluid, has been demonstrated to have compound effects on cartilage tissue in this manner in osteoarthritis. It was surprising to find that alginic acid, which is a polymer originating in algae and is not inherently present in animals, has effects such as these.

Rheumatoid arthritis is a type of autoimmune disease and has a different pathology than osteoarthritis. In rheumatoid arthritis, drugs having the function of a "disease modifying drug" that inhibits degeneration and destruction of joint tissue consist primarily of immunomodulators that act systemically in the manner of anti-TNFα antibodies and methotrexate. Although hyaluronic acid, which is a polysaccharide similar to alginic acid, is a therapeutic agent for osteoarthritis, it is only used in symptomatic therapy for joint pain in rheumatoid arthritis. Thus, even though therapeutic effects have been obtained for osteoarthritis with alginic acid, it was difficult to predict whether or not it has therapeutic effects in rheumatoid arthritis. It was therefore surprising to find that a highly safe and naturally-occurring polysaccharide polymer like alginic acid, commonly used in foods and pharmaceutical bases, functions as a disease modifying drug of rheumatoid arthritis by intra-articular injection.

Namely, the present invention provides a composition allowing the obtaining of therapeutic effects by injecting into a joint of a patient having a joint disease.

(1-1) A composition, which is used for treatment of a joint disease and which is injected into a joint, containing as an active ingredient thereof a low endotoxin monovalent metal salt of alginic acid.

(1-2) A composition, which is used for inhibition of cartilage degenerative changes and which is injected into a joint, containing as an active ingredient thereof a low endotoxin monovalent metal salt of alginic acid.

(1-3) A composition, which is used for cartilage protection and which is injected into a joint, containing as an active ingredient thereof a low endotoxin monovalent metal salt of alginic acid.

(1-4) A composition, which is used for cartilage repair and which is injected into a joint, containing as an active ingredient thereof a low endotoxin monovalent metal salt of alginic acid.

(1-5) A composition, which is used for suppression of joint pain and which is injected into a joint, containing as an active ingredient thereof a low endotoxin monovalent metal salt of alginic acid.

(1-6) A composition, which is used for inhibition of joint inflammation and which is injected into a joint, containing as an active ingredient thereof a low endotoxin monovalent metal salt of alginic acid.

(1-7) A composition, which is used for improvement of joint function and which is injected into a joint, containing as an active ingredient thereof a low endotoxin monovalent metal salt of alginic acid.

(1-8) A composition, which is used for treatment of osteoarthritis and which is injected into a joint, containing as an active ingredient thereof a low endotoxin monovalent metal salt of alginic acid.

(1-9) A composition, which is used for treatment of frozen shoulder and which is injected into a joint, containing as an active ingredient thereof a low endotoxin monovalent metal salt of alginic acid.

(1-10) A composition, which is used for suppression of joint pain associated with rheumatoid arthritis and which is injected into a joint, containing as an active ingredient thereof a low endotoxin monovalent metal salt of alginic acid.

(1-11) A composition for treating rheumatoid arthritis, which is injected into a joint, containing as an active ingredient thereof a low endotoxin monovalent metal salt of alginic acid.

(1-12) A composition for inhibiting degeneration of synovial tissue in rheumatoid arthritis, which is injected into a joint, containing as an active ingredient thereof a low endotoxin monovalent metal salt of alginic acid.

(1-13) A composition for inhibiting joint destruction in rheumatoid arthritis, which is injected into a joint, containing as an active ingredient thereof a low endotoxin monovalent metal salt of alginic acid.

(1-14) A composition for intra-articular injection having the effect of alleviating, improving or curing symptoms associated with joint disease, which contains as an active ingredient thereof a low endotoxin monovalent metal salt of alginic acid.

(1-15) The composition described in (1-14) above, wherein the effect of alleviating, improving or curing symptoms associated with joint disease is at least one effect selected from the group consisting of inhibition of cartilage degenerative changes, cartilage protection, cartilage repair, suppression of joint pain, inhibition of joint inflammation, improvement of joint function, inhibition of synovial tissue degeneration, inhibition of osteochondral destruction and inhibition of joint destruction.

(1-16) The composition described in any of (1-1) to (1-15) above, wherein the monovalent metal salt of alginic acid is sodium alginate.

(1-17) The composition described in (1-16) above, wherein the sodium alginate is sodium alginate having a weight average molecular weight of 500,000 or more as determined by gel filtration chromatography.

(1-18) The composition described in any of (1-1) to (1-17) above, not containing cells (for example, cells for cartilage tissue regeneration).

(1-19) The composition described in any of (1-1) to (1-18) above, not containing a curing agent of a monovalent metal salt of alginic acid.

(1-20) A composition for treating rheumatoid arthritis, which is injected into a joint, containing as an active ingredient thereof a low endotoxin sodium alginate having a weight average molecular weight of 500,000 or more as determined by gel filtration chromatography, wherein the composition does not contain cells and is non-curable.

Moreover, the present invention provides a treatment method for joint disease and symptoms associated therewith.

(2-1) A method of treating a joint disease comprising: injecting into a joint a composition containing as an active ingredient thereof a low endotoxin monovalent metal salt of alginic acid.

(2-2) A method of inhibiting cartilage degenerative changes comprising: injecting into a joint a composition containing as an active ingredient thereof a low endotoxin monovalent metal salt of alginic acid.

(2-3) A method of protecting cartilage comprising: injecting into a joint a composition containing as an active ingredient thereof a low endotoxin monovalent metal salt of alginic acid.

(2-4) A method of repairing cartilage comprising: injecting into a joint a composition containing as an active ingredient thereof a low endotoxin monovalent metal salt of alginic acid.

(2-5) A method of suppressing joint pain comprising: injecting into a joint a composition containing as an active ingredient thereof a low endotoxin monovalent metal salt of alginic acid.

(2-6) A method of inhibiting joint inflammation comprising: injecting into a joint a composition containing as an active ingredient thereof a low endotoxin monovalent metal salt of alginic acid.

(2-7) A method of improving joint function comprising: injecting into a joint a composition containing as an active ingredient thereof a low endotoxin monovalent metal salt of alginic acid.

(2-8) A method of treating osteoarthritis comprising: injecting into a joint a composition containing as an active ingredient thereof a low endotoxin monovalent metal salt of alginic acid.

(2-9) A method of treating frozen shoulder comprising: injecting into a joint a composition containing as an active ingredient thereof a low endotoxin monovalent metal salt of alginic acid.

(2-10) A method of suppressing joint pain associated with rheumatoid arthritis comprising: injecting into a joint a composition containing as an active ingredient thereof a low endotoxin monovalent metal salt of alginic acid.

(2-11) A method of treating rheumatoid arthritis comprising: injecting into a joint a composition containing as an active ingredient thereof a low endotoxin monovalent metal salt of alginic acid.

(2-12) A method of inhibiting degeneration of synovial tissue in rheumatoid arthritis comprising: injecting into a joint a composition containing as an active ingredient thereof a low endotoxin monovalent metal salt of alginic acid.

(2-13) A method of inhibiting joint destruction in rheumatoid arthritis comprising: injecting into a joint a composition containing as an active ingredient thereof a low endotoxin monovalent metal salt of alginic acid.

(2-14) A method of alleviating, improving or curing symptoms associated with joint disease comprising: injecting into a joint a composition containing as an active ingredient thereof a low endotoxin monovalent metal salt of alginic acid.

(2-15) The method described in (2-14) above, wherein the effect of alleviating, improving or curing symptoms associated with joint disease is at least one effect selected from the group consisting of inhibition of cartilage degenerative changes, cartilage protection, cartilage repair, suppression of joint pain, inhibition of joint inflammation, improvement of joint function, inhibition of synovial tissue degeneration, inhibition of osteochondral destruction and inhibition of joint destruction.

(2-16) The method described in any of (2-1) to (2-15) above, wherein the monovalent metal salt of alginic acid is sodium alginate.

(2-17) The method described in (2-16) above, wherein the sodium alginate is sodium alginate having a weight average molecular weight of 500,000 or more as determined by gel filtration chromatography.

(2-18) The method described in any of (2-1) to (2-17) above, wherein the composition does not contain cells (such as cells for regenerating cartilage tissue).

(2-19) The method described in any of (2-1) to (2-18) above, wherein the composition does not contain a curing agent of a monovalent metal salt of alginic acid.

(2-20) A method of treating rheumatoid arthritis comprising: injecting into a joint a composition containing as an active ingredient thereof a low endotoxin sodium alginate having a weight average molecular weight of 500,000 or more as determined by gel filtration chromatography, wherein the composition does not contain cells and is non-curable.

The composition for treating a joint disease of the present invention is able to inhibit the progression of joint disease and symptoms associated with joint disease, and alleviate or cure symptoms thereof by injecting into a joint in a liquid state. One aspect of the composition of the present invention demonstrates reparative, protective and degeneration inhibitory effects on mechanical damage of cartilage while also inhibiting inflammatory reactions and pain in joint tissue. Moreover, the composition demonstrates therapeutic effects for joint destruction by inhibiting degeneration of synovial tissue accompanying an autoimmune response and inhibiting osteochondral destruction. The composition contributes to improving joint function in joint disease through these combined effects. In particular, the composition is useful in the treatment of osteoarthritis, treatment of frozen shoulder, alleviation of joint pain in rheumatoid arthritis, and treatment of rheumatoid arthritis.

BRIEF DESCRIPTION OF THE DRAWINGS

FIG. 1 is a chart showing the criteria for scoring overall observations in a rabbit cartilage repair model of Example 1.

FIG. 2 is a chart showing the criteria for scoring the results of staining in a rabbit cartilage repair model of Example 1.

FIG. 3A-B show photographs of tissue staining of a control group A) (empty) in a rabbit cartilage repair model of Example 1. FIG. 3A shows the results after 4 weeks while FIG. 3B shows the results after 12 weeks. The results are shown for, moving from left to right, H-E staining, Safranin-O staining and type I collagen and type II collagen immunostaining.

FIG. 4A-B show photographs of tissue staining of a food grade alginate+cells group C) in a rabbit cartilage repair model of Example 1. FIG. 4A shows the results after 4 weeks while FIG. 4B shows the results after 12 weeks. The staining methods are the same as those of FIG. 3.

FIG. 5A-B show photographs of tissue staining of a purified alginate (no cells) group D) in a rabbit cartilage repair model of Example 1. FIG. 5A shows the results after 4 weeks while FIG. 5B shows the results after 12 weeks. The staining methods are the same as those of FIG. 3.

FIG. 6A-B show photographs of tissue staining of a purified alginate+cells group E) in a rabbit cartilage repair model of Example 1. FIG. 6A shows the results after 4 weeks while FIG. 6B shows the results after 12 weeks. The staining methods are the same as those of FIG. 3.

FIG. 7 shows the results of scoring overall observations and staining in a rabbit cartilage repair model of Example 1.

DISCLOSURE

Figure 8:
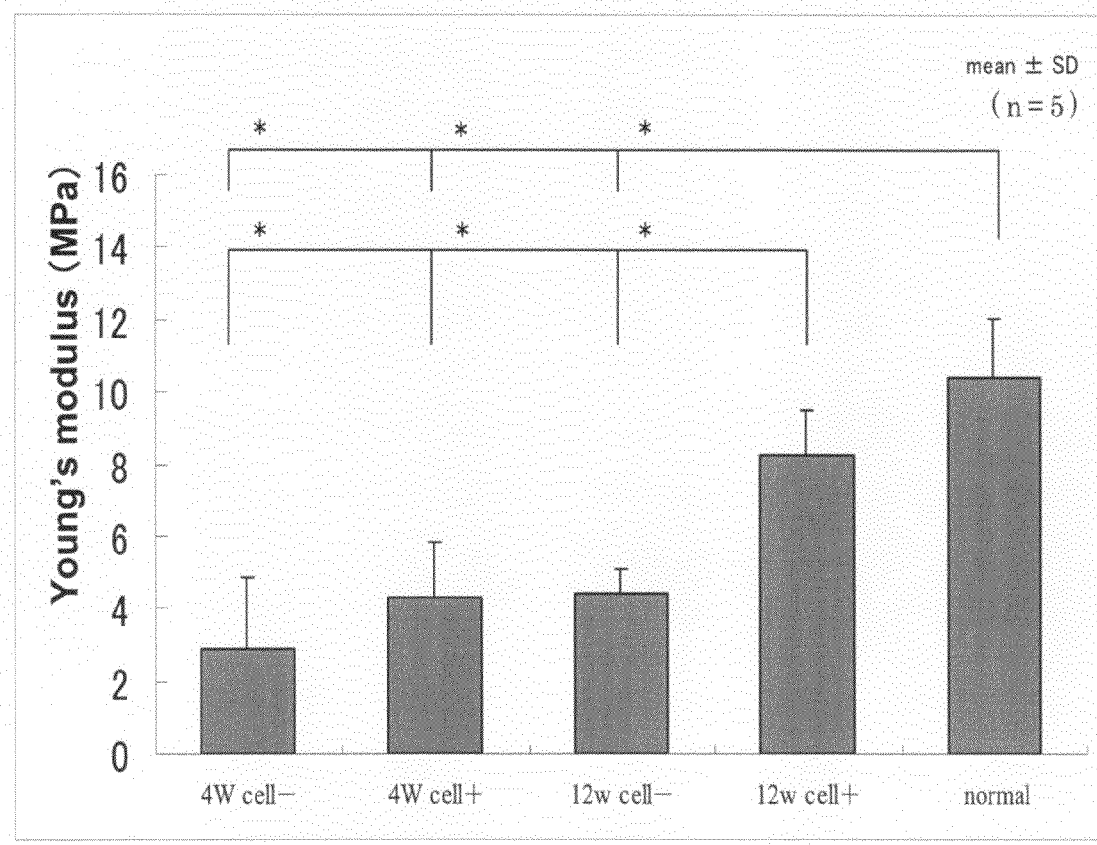
FIG. 8 is a graph showing the results of measuring mechanical strength for a purified alginate groups D) and E) in a rabbit cartilage repair model of Example 1.

Although the following provides a detailed explanation of the present invention, the following embodiments are intended to be exemplary for explaining the present invention, and the present invention can be carried out in various forms without deviating from the purport thereof.

1. Introduction

"Cartilage" is found in joints; thoracic wall; intervertebral discs; meniscus; tubular structure such as throat, respiratory tract and ears and so on, and is classified into three types consisting of hyaline cartilage, elastic cartilage and fibrous cartilage. For example, articular cartilage is classified as hyaline cartilage, is composed of chondrocytes, collagenous extracellular matrix, proteoglycan and water, and is free of vascular intervention. Hyaline cartilage is rich in type II collagen, and is stained by type II collagen antibodies. It is also characterized by being stained red by safranin-O stain used to stain proteoglycan. A "cartilage injury" refers to a state in which the cartilage has been damaged due to aging, trauma or other factors, and includes a state in which cartilage function has decreased, such as a decrease in the characteristic viscoelasticity of cartilage (which enables cartilage to slowly compress when subjected to a load and then slowly return to its original state when the load is removed) thereby bringing about impairment of the ability of the cartilage to support a load while maintaining mobility. The cartilage injury can also be observed in the disease such as osteoarthritis and rheumatoid arthritis.

In the present invention, "joint disease" refers to a disease that occurs due to cartilage, cartilage tissue and/or joint tissue (such as the synovial membrane, articular capsule or subchondral bone) having been injured by mechanical irritation or inflammatory response. "Joint disease treatment" refers to alleviating, improving and/or curing various symptoms of tissue that has been injured by mechanical irritation or inflammatory response. For example, in cases of osteoarthritis, there is compound occurrence of symptoms such as articular cartilage wear, degeneration of cartilage tissue, inflammation of the synovial membrane or pain associated with inflammation. On the other hand, in cases of frozen shoulder, symptoms primarily consist of inflammation of the synovial membrane and articular capsule as well as pain associated therewith, while cartilage wear and degeneration may not be observed. Although the mechanism of occurrence of rheumatoid arthritis is not fully understood, synovial tissue and cartilage tissue are thought to be destroyed by inflammatory cytokines resulting from an autoimmune response. In this manner, joint disease is a disease that presents with compound symptoms, and drugs for the treatment thereof are required to have compound effects, including protection of cartilage from wear, inhibition of degenerative changes in cartilage due to wear or inflammation, repair of cartilage injury lesions, inhibition of inflammation and pain, inhibition of synovial tissue degeneration, and inhibition of osteochondral destruction. The "composition containing a low endotoxin monovalent metal salt of alginic acid" of the present invention has the effects of protecting cartilage from mechanical irritation, inhibiting degenerative changes in cartilage caused by wear or inflammation, repairing cartilage injury lesions, inhibiting inflammation and pain of joint tissue, inhibiting synovial tissue degeneration, and inhibiting osteochondral destruction. As a result, the composition is able to inhibit the progress of joint disease, and alleviate, improve and/or cure symptoms. In particular, the composition is useful for treating osteoarthritis, treating frozen shoulder, alleviating joint pain associated with rheumatoid arthritis and treating rheumatoid arthritis.

In addition, "injecting into a joint" refers to injection of a liquid composition having fluidity into, for example, an articular cavity, synovial bursa or peritenon. In the case of using to treat osteoarthritis and rheumatoid arthritis, the composition is preferably injected into an articular cavity. Furthermore, although osteoarthritis and rheumatoid arthritis can occur in various joints of the body, including those of the knees, shoulders, hips, lower back, ankles, wrists and fingers, the composition of the present invention can be applied to any of these joints.

2. Monovalent Metal Salt of Alginic Acid

The "monovalent metal salt of alginic acid" contained in the composition for treating a joint disease of the present invention is a water-soluble salt formed by ion exchange between a hydrogen atom of carboxylic acid at position 6 of alginic acid and a monovalent metal ion such as $Na^+$ or $K^+$. Although specific examples of monovalent metal salts of alginic acid include sodium alginate and potassium alginate, sodium alginate acquirable as a commercially available product is particularly preferable.

The "alginic acid" used in the present invention is a biodegradable, high molecular weight polysaccharide that is a polymer obtained by linearly polymerizing two types of uronic acids in the form of D-mannuronic acid (M) and L-gluronic acid (G). More specifically, the alginic acid is a block copolymer in which a homopolymer fraction of D-mannuronic acid (MM fraction), homopolymer fraction of L-gluronic acid (GG fraction) and fraction in which D-mannuronic acid and L-gluronic acid are randomly arranged (MG fraction) are linked arbitrarily. The composite ratio of the D-mannuronic acid to the L-gluronic acid of the alginic acid (M/G ratio) mainly varies according to the type of algae or other organism serving as the origin thereof, is affected by the habitat and season of that organism, and extends over a wide range from a high G type having an M/G ratio of about 0.4 to a high M type having an M/G ratio of about 5.

A monovalent metal salt of alginic acid is a polysaccharide, and although it is difficult to accurately determine molecular weight, it generally has a weight average molecular weight of 10,000 to 10,000,000 and preferably 50,000 to 3,000,000. Sodium alginate having a weight average molecular weight of about 1,000,000 and 1,700,000 as determined by gel filtration chromatography demonstrated superior cartilage degenerative change inhibitory effects, cartilage protective effects, cartilage repair effects and joint pain inhibitory effects as compared with sodium alginate having a molecular weight of about 400,000. In the case of calculating the molecular weight of a polysaccharide by gel filtration chromatography, there is normally the potential for measurement error of 10 to 20%. For example, a molecular weight of 400,000 can fluctuate within the range of 320,000 to 480,000, a molecular weight of 500,000 can fluctuate within the range of 400,000 to 600,000, and a molecular weight of 1,000,000 can fluctuate within the range of 800,000 to 1,200,000. Thus, the preferable weight average molecular weight range of a monovalent metal salt of alginic acid for which effects on joint disease are particularly superior is at least 500,000 or more, more preferably 650,000 or more, and even more preferably 800,000 or more. In addition to production being difficult, since problems occur such as viscosity when preparing an aqueous solution being excessively high or solubility decreasing if the molecular weight is excessively high, the weight average molecular weight is preferably 5,000,000 or less and more preferably 3,000,000 or less.

Since high molecular weight substances derived from a natural origin typically do not have a single molecular weight, but rather consist of an aggregate of molecules having various molecular weights, molecular weight is measured in the form of a molecular weight distribution having a certain range. A typical measurement technique is gel filtration chromatography. Typical examples of information obtained from molecular weight distribution as determined by gel filtration chromatography include weight average molecular weight (Mw), number average molecular weight (Mn) and variance ratio (Mw/Mn).

Weight average molecular weight emphasizes the contribution of average molecular weight of polymers having a large molecular weight, and is represented with the following formula:

$$Mw = \Sigma(WiMi)/W = \Sigma(HiMi)/\Sigma(Hi)$$

Number average molecular weight is calculated by dividing the total weight of polymers by the total number of polymers.

$$Mn = W/\Sigma Ni = \Sigma(MiNi)/\Sigma Ni = Z(Hi)/\Sigma(Hi/Mi)$$

Here, W represents the total weight of all polymers, Wi represents the weight of the ith polymer, Mi represents molecular weight at an ith elution time, Ni represents the number of molecular weights Mi, and Hi represents the height at the ith elution time.

Since cartilage regeneration effects (and particularly hyaline cartilage regeneration effects) at cartilage injury lesions, cartilage repair effects, effects inhibiting cartilage degenerative changes and/or cartilage protective effects in the treatment of a joint disease are considered to be largely contributed to by molecular species having large molecular weights, weight average molecular weight may be used as an indicator of molecular weight.

Differences in values according to the measurement method are known to occur in the measurement of molecular weights of high molecular weight substances derived from a natural origin (example of hyaluronic acid: Chikako Yomota et al., Bull. Natl. Health Sci., Vol. 117, pp. 135-139 (1999), Chikako Yomota et al., Bull. Natl. Health Sci., Vol. 121, pp. 30-33 (2003)). Methods for measuring the molecular weight of alginate described in the literature include a method in which molecular weight is calculated from intrinsic viscosity, and a method in which molecular weight is calculated by Size Exclusion Chromatography with Multiple Angle Laser Light Scattering Detection (SEC-MALLS) (ASTM F2064-00 (2006), published by ASTM International). Furthermore, it is also described in the literature that in the measurement of molecular weight by size exclusion chromatography (gel filtration chromatography), calculation from a calibration curve using pullulan for the standard substance is insufficient, and it is recommended that measurement of molecular weight be used in combination with multiple angle laser light scattering detector (MALLS) (namely, measurement by SEC-MALLS). In addition, there are also examples of the use of molecular weights determined by SEC-MALLS being used as catalog specifications of alginates (FMC Biopolymer Inc., PRONOVA™ Sodium Alginates Catalog).

The inventors of the present invention found there to be differences in the therapeutic effects of sodium alginate having different molecular weights in an OA model, and measured the molecular weights of these alginates by gel filtration chromatography and SEC-MALLS. As a result, molecular weights determined by gel filtration chromatography were determined to demonstrate a higher correlation with viscosity and therapeutic effects of the alginates. Namely, it was newly found that rather than the generally recommended SEC-MALLS method, molecular weight determined by gel filtration chromatography was found to be suitable as a parameter for specifying the preferable molecular weight range of alginates used in a composition for treatment of a joint disease. Thus, in the case of specifying the molecular weight of an alginate in the present specification, that molecular weight is the weight average molecular weight as calculated by gel filtration chromatography unless specifically stated otherwise.

The preferable conditions for gel filtration chromatography as indicated in the examples. A typical condition consists of the use of a calibration curve using pullulan for the standard substance. Pullulan having a molecular weight of at least 1,600,000, 788,000, 404,000, 212,000 and 112,000 is preferably used for the pullulan used for the standard substance. In addition, the eluate (200 mM sodium nitrate solution), column conditions and the like can also be specified. Column conditions preferably consist of using polymethacrylate resin-based filler and using at least one column having a molecular weight cutoff of 10,000,000 or more. A typical example of a column is the TSKgel GMPWx1 (diameter: 7.8 mm×300 mm) (Tosoh Corp.).

Although a monovalent metal salt of alginic acid has a large molecular weight and high viscosity when initially isolated from brown algae, molecular weight decreases and viscosity lowers during the course of undergoing heat-drying, freeze-drying, purification and the like. Thus, monovalent metal salts of alginic acid having different molecular weights can be produced by suitably controlling the temperature in each step of production. Monovalent metal salts of alginic acid having a high molecular weight are obtained by controlling the temperature in each of step of production to be somewhat low, while monovalent metal salts of alginic acid having a low molecular weight are obtained by controlling the temperature in each step of production to be somewhat high. In addition, monovalent metal salts of alginic acid having different molecular weights can also be produced by a technique such as suitably selecting the brown algae used for the raw material, or fractionating according to molecular weight in the production process. Moreover, a monovalent metal salt of alginic acid having a target molecular weight can also be obtained by mixing a monovalent metal salt of alginic acid produced according to various production processes with a different lot of monovalent metal salt of alginic acid having a different molecular weight or viscosity after having measured the molecular weight or viscosity thereof.

Although the alginic acid used in the present invention may be of a natural origin or synthetic, it is preferably derived from a natural origin. Examples of naturally-occurring alginic acids include those extracted from brown algae. Although brown algae containing alginic acid are prominently found along seacoasts throughout the world, algae that can actually be used as raw materials of alginic acid are limited, with typical examples thereof including *Lessonia* species found in South America, *Macrocystis* species found in North America, *Laminaria* and *Ascophyllum* species found in Europe, and *Durvillea* species found in Australia. Examples of brown algae serving as raw materials of alginic acid include *Lessonia* species, *Macrocystis* species, *Laminaria* species, *Ascophyllum* species, *Durvillea* species, *Eisenia* species and *Ecklonia* species.

3. Endotoxin Reduction Treatment

The monovalent metal salt of alginic acid contained in the composition for treatment of a joint disease of the present invention is a low endotoxin monovalent metal salt of alginic acid. Low endotoxin refers to that in which the endotoxin level thereof has been substantially lowered to an extent that does not induce inflammation or fever. Namely, the monovalent metal salt of alginic acid has been subjected to endotoxin reduction treatment. It was surprisingly found that by subjecting to this endotoxin reduction treatment, in addition to being able to enhance the cartilage regenerative action of the composition when applied to a cartilage injury lesion, the regeneration of subchondral bone can be promoted and mechanical strength of the affected area can be enhanced. Namely, by using low endotoxin alginic acid in the composition of the present invention, a composition can be obtained having high bioaffinity, and not inducing degeneration and inflammatory responses in surrounding cartilage.

Endotoxin reduction treatment can be carried out by a known method or a method complying therewith. For example, this treatment can be carried out by the method of Suga et al. involving purification of sodium hyaluronate (see, for example, Japanese Patent Application Laid-open No. H9-324001), the method of Yoshida et al. involving purification of β1,3-glucan (see, for example, Japanese Patent Application Laid-open No. H8-269102), the method of William et al. involving purification of a biopolymer such as alginate or gellan gum (see, for example, Published Japanese Translation No. 2002-530440 of PCT International Publication), the method of James et al. involving purification of polysaccharide (see, for example, International Publication No. 93/13136 pamphlet), the method of Lewis et al. (see, for example, U.S. Pat. No. 5,589,591), the method of Hermanfranck et al. involving purification of alginate (see, for example, Appl. Microbiol. Biotechnol. (1994), 40:638-643) or a method complying therewith. The endotoxin reduction treatment of the present invention is not limited thereto, but rather can be carried out by a known method such as cleaning, purification using filtration with filter (endotoxin removing filter or electrification filter), ultrafiltration or a column (such as an endotoxin adsorption affinity column, gel filtration column or ion exchange column), adsorption to a hydrophobic substance, resin or activated carbon and the like, organic solvent treatment (such as extraction with an organic solvent or precipitation or deposition by addition of organic solvent), surfactant treatment (see, for example, Japanese Patent Application Laid-open No. 2005-036036) or a suitable combination thereof. A known method such as centrifugal separation may be suitably combined with these treatment steps. Endotoxin reduction treatment is preferably suitably selected according to the type of alginic acid.

Endotoxin level can be confirmed by a known method, and can be measured using a known method such as a method using a limulus reagent (LAL) or method using an Endospecy (registered trademark) ES-24S set (Seikagaku Corp.). Although there are no particular limitations on the endotoxin treatment method of the alginic acid contained in the composition of the present invention, the endotoxin content of the monovalent metal salt of alginic acid in the case of measuring endotoxin using a limulus reagent (LAL) is preferably 500 endotoxin units (EU)/g or less, more preferably 100 EU/g or less, even more preferably 50 EU/g or less and particularly preferably 30 EU/g or less as a result thereof.

Sodium alginate that has undergone endotoxin reduction treatment can be acquired as commercially available products such as Sea Matrix (sterilized) (Kimica Corp., Mochida International Ltd.) and Pronova™ UP LVG (FMC).

4. Preparation of Solution of Monovalent Metal Salt of Alginic Acid

The composition for treating a joint disease of the present invention may be prepared by using a solution of a monovalent metal salt of alginic acid. The solution of a monovalent metal salt of alginic acid can be prepared by a known method or method complying therewith. Namely, the monovalent metal salt of alginic acid used in the present invention can be produced by a known method such as an acid method or calcium method using the previously described brown algae. More specifically, after extracting from these brown algae using an alkaline aqueous solution such as aqueous sodium carbonate solution, for example, alginic acid be obtained by adding an acid (such as hydrochloric acid or sulfuric acid), and a salt of alginic acid can be obtained by ion exchange of the alginic acid. Endotoxin reduction treatment is then carried out as previously described. There are no particular limitations on the solvent of the alginic acid salt provided it is a solvent that can be applied in vivo, and examples of such solvents include purified water, distilled water, ion exchange water, Milli-Q water, physiological saline and phosphate-buffered saline (PBS).

These are preferably sterilized and preferably subjected to endotoxin reduction treatment. For example, Milli-Q water can be used after sterilizing by filtration. In addition, the procedure for obtaining the composition of the present invention is preferably carried out in an environment having low levels of endotoxins and bacteria. For example, the procedure is preferably carried out on a clean bench using sterilized apparatuses, and the apparatuses used may be treated with a commercially available endotoxin removal agent.

In the case of producing a composition as described above using a monovalent metal salt of alginic acid that has been purified to a preferable endotoxin level, the endotoxin content of the composition is normally 500 EU/g or less, more preferably 300 EU/g or less and particularly preferably 150 EU/g or less.

5. Viscosity of Composition for Treating Joint Disease

Although there are no particular limitations on the viscosity of the composition for treating a joint disease of the present invention in the case of injecting it into a joint provided therapeutic effects for joint disease are obtained, it is preferably 100 to 20000 mPa·s. For example, the composition for treating a joint disease of the present invention can be adjusted to a suitable viscosity using the above-mentioned solvent. If viscosity is within this range, the composition for treating a joint disease of the present invention can be injected with a syringe and the like. The viscosity is preferably 150 to 15000 mPa·s, more preferably 200 to 10000 mPa·s, and particularly preferably 250 to 6000 mPa·s. The use of a suitable viscosity makes it possible to demonstrate the effect of compensating for cushioning function of synovial fluid, thereby making it possible to demonstrate the effect of treating a joint disease in a state of being dispersed in synovial fluid.

The viscosity of the composition for treating a joint disease can be adjusted by, for example, controlling the concentration of alginic acid in the solution of a monovalent metal salt of alginic acid or controlling the molecular weight of the alginic acid.

The viscosity of the solution of the monovalent metal salt of alginic acid increases when the concentration of alginic acid in the solution is high and decreases when the concentration of alginic acid in the solution is low. Although unable to be stated unequivocally as a result of being affected by molecular weight, the preferable concentration of alginic acid in the solution of the monovalent metal ion of alginic acid is roughly 0.2 to 5% w/v, more preferably 0.5 to 3% w/v and particularly preferably 1 to 2.5% w/v.

A monovalent metal salt of alginic acid having a high molecular weight can be selected to obtain a composition having high viscosity from a solution of a monovalent metal salt of alginic acid having a low concentration. Since the viscosity of the solution of a monovalent metal salt of alginic acid is affected by the M/G ratio, an alginic acid can be suitably selected that has an M/G ratio more preferable for viscosity of the solution and the like. The M/G ratio of alginic acid used in the present invention is about 0.4 to 4.0, preferably about 0.8 to 3.0 and more preferably about 1.0 to 1.6.

As previously described, since the M/G ratio is determined primarily by the type of algae, the type of brown algae used for the raw material has an effect on the viscosity of the solution of the monovalent metal salt of alginic acid. The alginic acid used in the present invention is preferably derived from brown algae of the genii *Lessonia*, *Macrocystis*, *Laminaria*, *Ascophyllum* and *Durvillea*, more preferably derived from brown algae of the genii *Lessonia*, and particularly preferably brown algae of *Lessonia nigrescens*.

6. Formulation and Application of a Composition for Treating Joint Disease Containing a Monovalent Metal Salt of Alginic Acid The composition for treating a joint disease of the present invention is used to treat a joint disease by injecting into a joint of a human or non-human mammal such as a cow, monkey, bird, cat, mouse, rat, guinea pig, hamster, pig, dog, rabbit, sheep or horse.

The form of the composition for treating a joint disease of the present invention is a fluid liquid, namely a solution. In the present invention, the phrase "having fluidity" refers to the having of a property that causes the form thereof to change to an amorphous form. For example, the composition preferably has fluidity such that it is able to be injected into an affected area. The composition of the present invention in the form of a solution can be easily applied to a joint with a syringe, gel pipette or special-purpose syringe.

The composition for treating a joint disease of the present invention demonstrates therapeutic effects on joint disease in joint diseases such as osteoarthritis, frozen shoulder and rheumatoid arthritis by having cartilage repair effects, inhibitory effects on cartilage degenerative changes, cartilage protective effects, inhibitory effects on inflammation of joint tissue, inhibitory effects on pain attributable to inflammation of joint tissue, inhibitory effects on synovial tissue degeneration and/or inhibitory effects on osteochondral destruction. The composition for treating a joint disease of the present invention inhibits joint destruction and improves joint function through these combined effects.

One aspect of the composition for treating a joint disease of the present invention is a composition for treating osteoarthritis. In the case a cartilage injury extends over a wide area of articular cartilage in the manner of osteoarthritis, or when desiring to treat a type of cartilage injury frequently observed in a comparatively early stage of osteoarthritis such that smoothness of the cartilage surface is disturbed and degenerative changes have begun even though well-defined cartilage defects have not yet occurred, the composition of the present invention is preferably applied by injecting into an articular cavity and allowing to disperse throughout the synovial fluid. Contact of a monovalent metal salt of alginic acid with a cartilage injury lesion promotes repair of the joint at the cartilage injury lesion, inhibits degenerative changes caused by inflammation and wear, and protects the cartilage. In addition, as a result of the active ingredient in the form of a monovalent metal salt of alginic acid being dispersed throughout the synovial fluid, inflammatory responses of surrounding tissue, including synovial tissue, are inhibited and effects that suppress pain are demonstrated. At the same time, the presence of a monovalent metal salt of alginic acid within synovial fluid fulfills the role of compensating for the function of synovial fluid by serving as a cushion and lubricant.

Another aspect of the composition for treating a joint disease of the present invention is a composition for treating frozen shoulder (periarthritis humeroscapularis). Frozen shoulder presents primarily with inflammation of the synovial membrane and articular capsule coupled with pain associated therewith, and cartilage wear and degeneration may not be observed. Since a monovalent metal salt of alginic acid demonstrates the effects of inhibiting inflammatory responses of surrounding tissue, including synovial tissue and suppressing pain, frozen should can be treated by administering the composition of the present invention into the shoulder articular cavity, subacromial bursa or biceps muscle tendon sheath.

Another aspect of the composition for treating a joint disease of the present invention is a composition for suppressing joint pain. Joint pain is frequently a problem in rheumatoid arthritis in addition to osteoarthritis, frozen shoulder and the like as previously described. A preferable aspect of the present invention is a composition for treating joint pain associated with rheumatoid arthritis, and is particularly preferably a composition for suppressing knee joint pain associated with chronic rheumatoid arthritis.

Although the mechanism of occurrence of rheumatoid arthritis is not yet fully understood, synovial tissue and cartilage tissue are thought to be destroyed by inflammatory cytokines resulting from an autoimmune response. Since a monovalent metal salt of alginic acid demonstrates effects that inhibit inflammatory responses of surrounding tissue, including synovial tissue and suppress pain, the composition of the present invention is able to inhibit inflammatory responses and suppress pain associated therewith by administering into a joint suffering from rheumatoid arthritis.

One aspect of the composition for treating a joint disease of the present invention is a composition for treating rheumatoid arthritis. The composition of the present invention inhibits osteochondral destruction and degeneration of synovial tissue accompanying an autoimmune response. In addition, when degeneration of joint tissue occurs due to an autoimmune response, the joint is no longer able to demonstrate its inherent smooth movement, thereby resulting in mechanical injury to cartilage in the same manner as osteoarthritis. The composition of the present invention promotes joint repair of cartilage injuries and protects cartilage and inhibits degenerative changes in cartilage caused by inflammation and wear. The composition of the present invention demonstrates therapeutic effects by inhibiting joint destruction in rheumatoid arthritis through these combined effects.

Another aspect of the composition for treating a joint disease of the present invention is a composition for alleviating, improving and/or curing various symptoms associated with a joint disease. In a joint disease, cartilage, cartilage tissue and/or joint tissue (such as synovial membrane, articular capsule or subchondral bone) are injured by mechanical irritation or inflammatory response, and compound symptoms occur such as wear of articular cartilage, degenerative changes in cartilage tissue due to mechanical irritation along with inflammatory responses, inflammation of the synovial membrane and other joint tissue, joint pain attributable to inflammation, synovial tissue degeneration, and osteochondral destruction.

Since the composition of the present invention contains as an active ingredient thereof a low endotoxin monovalent metal salt of alginic acid, it has the multiple effects of protecting cartilage from mechanical irritation, inhibiting degenerative changes in cartilage caused by wear and inflammation, repairing cartilage injury lesions, inhibiting inflammation of joint tissue and pain, inhibiting synovial tissue degeneration, and inhibiting osteochondral destruction. As a result, the composition of the present invention is able to inhibit the progress of a joint disease, and alleviate, improve and/or cure symptoms. In addition, the composition for treating a joint disease of the present invention has the effect of improving joint function through alleviation, improvement and/or curing symptoms thereof. Improvement of joint function refers to improving joint range of movement, improving movement carried out during the course of daily life and the like.

In the case of applying the composition for treating a joint disease of the present invention by injecting into a joint, the dose is suitably determined according to amount of synovial fluid of the joint into which the composition is to be injected, and although there are no particular limitations thereon, in the case of administering to a human knee joint or shoulder joint, the dose is normally 1 to 5 mL and more preferably 2 to 3 mL. In addition, the administration method may consist of, for example, administering in five consecutive administrations at one week intervals, followed by continuous administrations every 2 to 4 weeks. Although there are no particular limitations on the dose, the dose can be suitably adjusted according to the symptoms and effects. For example, an administration method may be adopted in which administration is suitably continued once every two weeks, once every month, once every two months, once every three months or once every six months. Since alginic acid is inherently not present in the body, animals do not have an enzyme capable of specifically breaking down alginic acid. Although alginic acid is normally gradually decomposed by hydrolysis in an animal body, since its decomposition in the body is slow in comparison with polymers such as hyaluronic acid, it can be expected to sustain long-term effects in the case of being administered into a joint.

The composition for treating a joint disease of the present invention contains as an active ingredient thereof a low endotoxin monovalent metal salt of alginic acid. The inventors of the present invention found for the first time that alginic acid itself demonstrates therapeutic effects on cartilage tissue and joint tissue in the case of administering alginic acid into a joint of the body. A monovalent metal salt of alginic acid preferably refers to sodium alginate, and more preferably to sodium alginate having a weight average molecular weight of 500,000 or more as determined by gel filtration chromatography. The containing of alginic acid as an active ingredient means that alginic acid is contained in an amount that enables it to demonstrate therapeutic effects on cartilage tissue and joint tissue when applied to an affected area, and that amount is preferably at least 0.1% w/v or more of the entire composition, more preferably 0.5% w/v or more, and particularly preferably 1 to 3% w/v.

The composition for regenerating cartilage or treating a cartilage disease of the present invention can also contain other pharmaceutically active ingredients and components ordinarily used in pharmaceuticals, such as commonly used stabilizers, emulsifiers, osmotic pressure adjusters, buffers, isotonic agents, preservatives, pain relievers or colorants as necessary.

Furthermore, in one aspect of the present invention, the composition of the present invention does not contain a component demonstrating pharmacological action on cartilage or joint tissue other than a low endotoxin monovalent metal salt of alginic acid. A composition containing as an active ingredient thereof only a low endotoxin monovalent metal salt of alginic acid is also able to demonstrate adequate effects for treating a joint disease.

For example, it is preferable to use a composition not containing cells to facilitate the surgical procedure as well as reduce the risk of infection by viruses and the like attributable to the body or the culturing process without placing an excessive burden on the body through such procedures as harvesting chondrocytes, periosteum or bone marrow. Cells specifically refer to cells for regenerating cartilage tissue, examples of which include bone marrow mesenchymal stem cells, bone marrow mesenchymal stromal cells, cartilage precursor cells, chondrocytes, synoviocytes, erythropoietic stem cells and ES cells. The composition for treating a joint disease of the present invention is a composition having for an active ingredient thereof a low endotoxin monovalent metal salt of alginic acid, and is based on the finding that alginic acid itself has therapeutic effects on joint disease. A preferable example of a therapeutic composition is a cell-free composition for treating a joint disease injected into a joint containing as an active ingredient thereof low endotoxin sodium alginate having a weight average molecular weight of 500,000 or more as determined by gel filtration chromatography, that is able to demonstrate therapeutic effects superior to those of hyaluronic acid preparations used in the prior art.

The composition for treating a joint disease of the present invention preferable does not contain a curing agent for the monovalent metal salt of alginic acid. A curing agent for a monovalent metal salt of alginic acid refers to a component that causes curing or gelling of alginic acid in the presence of a monovalent metal salt of alginic acid in solution, examples of which include divalent or more metal ion compounds such as $Ca^{2+}$, $Mg^{2+}$, $Ba^{2+}$ or $Sr^{2+}$, and crosslinking reagents having 2 to 4 amino groups in a molecule thereof. Specific examples include $CaCl_2$, $MgCl_2$, $CaSO_4$ and $BaCl_2$, calcium gluconate and calcium alginate. When these components are contained to a degree that causes curing and/or gelling of alginic acid, injection with a syringe and the like becomes difficult due to gelling of alginic acid. As a result, problems occur such as obstruction of joint function due to solidification of a large amount of alginic acid within a joint. A curable composition is suitable for using by filling into a hole and so forth of a joint defect. On the other hand, in order to demonstrate combined therapeutic effects throughout all joint tissue of osteoarthritis or rheumatoid arthritis extending throughout the entire joint as in the manner of the composition of the present invention, the composition itself is preferably non-curable. Although typical drug solvents contain trace amounts of divalent metal ions, curing agents as referred to here are not applicable as long as they are added with the intention of curing and/or gelling a monovalent metal salt of alginic acid. A preferable aspect of the composition of the present invention is a composition not containing a curing agent of a monovalent metal salt of alginic acid to a degree that causes curing and/or gelling of alginic acid. In other words, a preferable aspect of the composition of the present invention is a non-curable composition.

Moreover, the present invention provides a method of treating joint disease using the composition for treating a joint disease of the present invention as described above. The method of treating joint disease of the present invention inhibits the progress of joint disease and alleviates, improves and/or cures symptoms by administering the composition for treating a joint disease of the present invention into a joint. Administration of the composition for treating a joint disease of the present invention into a joint inhibits the progress of joint disease and alleviates, improves and/or cures symptoms by demonstrating at least one of the effects selected from the group consisting of inhibition of cartilage degenerative changes, cartilage protection, cartilage repair, suppression of joint pain, inhibition of joint inflammation, inhibition of synovial tissue degeneration and inhibition of osteochondral destruction. Joint function is improved and joint destruction is inhibited through these combined effects.

There are no particular limitations on the method for applying the composition for treating a joint disease of the present invention to a joint, and for example, the composition may be injected directly into a joint with a syringe, gel pipette or special-purpose syringe. In the case of applying by injecting into a joint, an 18 to 27G needle is used preferably. "Injecting into a joint" refers to injecting a liquid composition having fluidity into an articular cavity, bursa or tendon sheath and the like. In the case of using to treat osteoarthritis or rheumatoid arthritis, the composition is preferably applied by injecting into an articular cavity. Furthermore, although osteoarthritis and rheumatoid arthritis may occur in various joints such as joints of the knee, shoulder, hip, lower back, ankle, wrist or fingers, the composition of the present invention can be applied to any of these joints.

In addition, concomitant drugs including antibiotics such as streptomycin, penicillin, tobramycin, amikacin, gentamicin, neomycin or amphotericin B or anti-inflammatory drugs such as aspirin, non-steroid anti-inflammatory drugs (NSAIDs) or acetaminophen, or steroid drugs may also be administered before, simultaneous to or after administration of the composition of the present invention. These drugs may also be used by mixing into the composition of the present invention.

7. Kit for Treating a Joint Disease

Moreover, the present invention provides a kit for treating a joint disease. This kit may include the composition for treating a joint disease of the present invention as described above, syringe, gel pipette, special-purpose filler, instructions and the like. A preferable specific example of a kit is that in which a monovalent metal salt of alginic acid is sealed in one compartment of a syringe composed of two integrally formed compartments divided by a partition, and a solution containing physiological saline as a dissolving solution is sealed in the other compartment, and is composed such that the partition between the compartments can be penetrated easily at the time of use to enable the contents of both compartments to be used by mixing and dissolving at the time of use. Another example of a kit is that a monovalent metal salt solution of alginic acid is sealed in a pre-filled syringe allowing it to be administered directly at the time of use without requiring a preparation procedure. Moreover, the kit can also contain concomitant drugs including antibiotics such as streptomycin, penicillin, tobramycin, amikacin, gentamicin, neomycin or amphotericin B or anti-inflammatory drugs such as aspirin, non-steroid antipyretic analgesic drugs (NSAIDs) or acetaminophen, or steroid drugs.

The use of this kit enables joint disease therapy to be carried out smoothly.

Furthermore, all publications cited in the present specification, such as prior art documents, laid-open patent applications, patent publications and other patent documents, are incorporated in their entirety in the present specification as references. In addition, the present specification incorporates the contents of the specifications of a Japanese patent application in the form of Japanese Patent Application No. 2007-277005 as well as International Patent Application PCT/JP2008/52999.

EXAMPLES

Although the following provides a detailed explanation of the present invention through examples thereof, the present invention is not limited to these examples.

Example 1

Rabbit Cartilage Repair Model (1) Production of Transplant Cells

Bone marrow mesenchymal stromal cells (BMSC) were isolated and cultured to obtain transplant cells. BMSC include erythropoietic cells and the like in addition to bone marrow mesenchymal stem cells. 10 mL of bone marrow were harvested from the tibia of four-month-old Japanese white rabbits followed by washing twice with Ca—Mg-free PBS (Gibco BRL Lab.) and suspending in DMEM-High Glucose (DMED-HG, Sigma Chemical, St. Louis, Mo.). Blood clots were removed with a cell strainer having a pore diameter of 70 μm (Falcon Co., Ltd.). The cells were then incubated while humidifying at 37° C. and 5% $CO_2$ in a 100 mm culture dish containing a culture medium consisting of DMEM-HG, 10% fetal bovine serum (FBS, Gibco, Life Technology, Grand Island, N.Y.) and 1% antibiotics (Penicillin-Streptomycin-Fungizone 100× concentrated, Cambrex Biosciences, Walkersville, Md.). The culture medium was replaced every three days and non-adherent cells were removed. After monolayer culturing the adherent cells for 10 to 14 days, the cells were removed with trypsin-EDTA (10 mM, Sigma, UK) and counted followed by subculturing every three days.

(2) Method (Procedure)

Forty female Japanese white rabbits (body weights: 2.6 to 2.9 kg) were anesthetized with isoflurane in $O_2$ gas and intravenous injection of pentobarbital (0.05 mg/kg) followed by intramuscular injection of antibiotic (Penicillin G, Meiji-Seika, Japan) and shaving of the legs. A 2 cm anteromedial incision was made in the skin and the trochlear groove was accessed using a medial parapatellar approach. Osteochondral defects (diameter: 5 mm, depth: 2 mm) were created in the femoral trochlea using a power drill (Rexon, Japan). The knees were then irrigated with physiological saline, the absence of bleeding into the defects was confirmed and the defects were allowed to dry.

In the present example, the experiment was conducted by dividing the animals into five groups.

A) Control group (empty)
B) Food grade alginate group (no cells)
C) Food grade alginate+cells ($2.5 \times 10^7$/mL) group
D) Purified alginate group (no cells)
E) Purified alginate+cells ($2.5 \times 10^7$/mL) group The defects were left untreated in the control group A). In addition, 2% w/v food grade sodium alginate solution was applied to the defects in the food grade alginate group B) (no cells). 2% w/v purified sodium alginate solution was applied to the defects in the purified alginate group D) (no cells). Sodium Alginate 500 (serial no. 199-09961) manufactured by Wako Pure Chemical Industries, Ltd. was used for the food grade alginate, while Sea Matrix (Sterilized) (serial no. B5Y01) manufactured by Kimica Corp., Mochida International Ltd. was used for the purified alginate. Moreover, the cells obtained in (1) were suspended in 2% w/v food grade sodium alginate solution or 2% w/v purified sodium alginate solution and applied to the articular cartilage defects in the food grade alginate+cells group C) and the purified alginate+cells group E), respectively. When endotoxin levels were measured using a commercially available LAL assay kit (Limulus Color KY Test Wako, Wako, Japan), the endotoxin level of the purified sodium alginate was 5.76 EU (endotoxin units)/g and that of the food grade sodium alginate was 75950 EU/g, thus indicating that the endotoxin level of the purified sodium alginate was far lower than that of the food grade sodium alginate. Namely, the purified sodium alginate had been subjected to endotoxin reduction treatment. In addition, the heavy metal content of the purified sodium alginate was 20 ppm or less, the lead sulfate content was 0.98% or less, and the arsenic content was 2 ppm or less.

The reason for making the concentration of the sodium alginate solutions 2% w/v was that this allows the viscosity to be adjusted to a level of 5000 to 6000 mPa·s suitable for the procedure. The rabbits were immobilized with the defects facing upward, and each composition was applied to the defects using a gel pipette.

Since the viscosity of the sodium alginate solution was suitable in groups B) through E), the sodium alginate solutions did not flow out of the defects despite conditions facilitating flow due to synovial fluid. Subsequently, approximately 0.5 ml of 100 mM $CaCl_2$ solution was slowly and continuously applied over the course of 10 seconds to the surface of the graft using a 27G syringe. The surface layer of the graft gelled immediately and the cells did not leave the affected area. The $CaCl_2$ solution was washed with physiological saline. Further immobilization was not required and the affected area was sutured following the procedure. The rabbits were able to move freely.

The subject rabbits were sacrificed by intravenous injection of an excessive dose of pentobarbital at 4 weeks or 12 weeks after the procedure. The distal ends of the femurs were excised with a power saw.

(Overall Observations)

The overall appearance was observed macroscopically and scored. Overall appearance was scored according to the criteria of FIG. 1 with reference to the method of Gabriele, G. et al. (Biomaterial, 21 (2000), 2561-2574).

(Staining)

Subsequently, the specimens were fixed with paraformaldehyde, decalcified and embedded in paraffin. Sections located 5 μm from the center of the defect were stained with Safranin-O, H-E stain and immunostained with anti-type I collagen and anti-type II collagen. The scoring system described in FIG. 2 was used to evaluate the newly formed cartilaginous tissue and the tissue was evaluated microscopically. Independent blinded observers performed the scoring.

(Measurement of Mechanical Strength)

The mechanical strength of the affected area was measured using an indentation test. The specimens were firmly clamped with the femuropatellar joint facing upward, and the test was carried out at room temperature. The indentator was automatically moved toward the center of the regenerated cartilage and the displacement (mm) was recorded relative to the load (N). The thickness of the regenerated tissue was measured from histological sections. Young's modulus was then obtained from the linear region of the load-displacement curves.

(3) Results

The results of staining are shown in FIG. 3 to FIG. 6. As a result of H-E staining, Safranin-O staining and anti-type II collagen immunostaining, the most prominent formation of hyaline cartilage and type II collagen in comparison with the other groups was confirmed in the purified alginate+cells group E) (FIG. 6) at an early stage 4 weeks after the procedure. Roughly 80% of the cartilage was observed to be regenerated at 12 weeks after the procedure. The formation of subchondral bone was extremely favorable based on the results of H-E staining. Safranin-O staining revealed the formation of proteoglycan, and the formation of an extracellular matrix was also able to be confirmed. On the other hand, there was hardly any formation of fibrous cartilage observed based on the results of H-E staining and anti-type I collagen immunostaining.

The purified alginate (no cells) group D) (FIG. 5) demonstrated favorable formation of hyaline cartilage, type II collagen and subchondral bone as compared with the food grade alginate+cells group C) (FIG. 4). In group D), in which cells were not embedded, cartilage regeneration was surprisingly found to have been obtained by hyaline chondrocytes. In addition, it also unexpectedly found that group D) in which cells were not embedded demonstrated a superior ability to regenerate cartilage injury as compared with group C) in which cells were embedded.

On the other hand, there was hardly any neogenesis of cartilage and type II collagen observed in control group A) (FIG. 3) in which the defects were left untreated.

The evaluation results obtained by macroscopically scoring the overall appearance (Macro) and the evaluation results obtained by scoring observations based on the staining described above (Histological) are shown in FIG. 7.

The total scores obtained by combining the Macro and Histological scores in week 12 consisted of 22.71 for the purified alginate+cells group E), 19.57 for the purified alginate (no cells) group D), 14.75 for the food grade alginate+cells group C), 10.25 for the food grade alginate (no cells) group B), and 8.43 for the control group A) (empty). Thus, the purified alginate+cells group E) demonstrated the highest score followed by the purified alginate (no cells) group D) and the food grade alginate+cells group C) in that order. It was completely unexpected that group D) in which cells were not embedded yielded a higher total score, and thereby demonstrating superior ability to regenerate cartilage in cartilage injuries, as compared with group C) in which cells were embedded.

The scoring results for both macroscopic evaluation of overall appearance (Macro total) and evaluation by staining (Histological total) were the highest in the purified alginate+cells group E) in the same manner as described above, and the next highest score was observed in the purified alginate (no cells) group D).

In looking at the Macro evaluation parameters, groups D) and E), in which purified alginate was used, were superior for all the parameters of edge integration (new tissue relative to native cartilage), smoothness of cartilage surface, cartilage surface, degree of filling, and color of cartilage, opacity or translucency of the neocartilage as compared with groups B) and C) in which food grade alginate was used.

In looking at the Histological evaluation parameters, groups D) and E), in which purified alginate was used, demonstrated higher scores than groups B) and C), in which food grade alginate was used, for the parameters of nature of predominant tissue, surface regularity, structural integrity and homogeneity, thickness, bonding to adjacent cartilage, degenerative changes in adjacent cartilage and inflammatory response.

On the basis of these findings, groups D) and E) demonstrated extremely favorable formation of chondrocytes and cartilage tissue in a cartilage injury, including the formation of hyaline cartilage, type II collagen and subchondral bone. There was hardly any formation of fibrous cartilage observed.

Bonding of the regenerated tissue to host tissue using purified alginate was also favorable, there was little degeneration or inflammation in adjacent cartilage, and bioaffinity was determined to be high.

The results of measuring mechanical strength for the purified alginate groups D) and E) are shown in FIG. 8.

As a result of measuring mechanical strength for the purified alginate groups, the mechanical strength in the purified alginate+cells group E) was a Young's modulus of 8 versus a Young's modulus of 10 in normal cartilage tissue, thus indicating that strength had recovered to nearly a normal, injury-free state. This finding also supported the claim that the composition of the present invention embedded with cells has superior mechanical strength, and is favorable with respect to regeneration of strong hyaline cartilage and the formation of subchondral bone.

Example 2

Measurement of Molecular Weight Distribution of Purified Sodium Alginate (1) Method The molecular weight distribution of purified sodium alginate was measured by gel filtration chromatography under the conditions indicated below.

Column: TSKgel GMPW×1, 2 columns+TSKgel G2500PW×1, 1 column (Tosoh Corp.) (diameter 7.8 mm×300 mm×3 columns)

Column temperature: 40° C.
Eluate: 200 mM aqueous sodium nitrate solution
Sample concentration: 0.05%
Flow rate: 1.0 mL/min
Injection volume: 200 μL
Detector: RI (differential refractometer)
Standards: Pullulan, glucose (molecular weights: 1,600,000, 788,000, 404,000, 212,000, 112,000, 47,300, 22,800, 11,800, 5900, 180)

(2) Results

TABLE 1

| Measurement sample | Number average molecular weight Mn | Weight average molecular weight Mw | Variance ratio Mw/Mn | (Reference) Viscosity of 1% aqueous solution |
|---|---|---|---|---|
| Purified sodium alginate (Kimica Corp., Mochida International Ltd., Sea Matrix ™ (sterilized), Serial No. B5Y01) | 430,000 | 1,700,000 | 4.0 | 400 to 500 mPa·s |
| Purified sodium alginate (FMC Biopolymer AS, Pronova ™ SLG20) | 66,000 | 440,000 | 6.6 | 20 to 100 mPa·s |

(3) Discussion

The weight average molecular weight of the purified sodium alginate used in the rabbit cartilage repair model of Example 1 was 1,700,000 as measured using the method described above. As indicated in Example 1, the sodium alginate demonstrated hyaline cartilage regenerative effects in the rabbit cartilage repair model both with and without cells. On the other hand, although a similar experiment was conducted using low endotoxin alginic acid (Pronova™ LVG, currently Pronova™ UP LVG, FMC Biopolymer Inc.) as described in Reference 3, it is disclosed that fibrous cartilage is formed in the case of applying only alginic acid not containing cells to a cartilage defect. Furthermore, the sterilized version of Pronova™ LVG is designated as Pronova™ SLG20, the weight average molecular weight thereof as determined by the method described above was 440,000. Although Sea Matrix™ and Pronova™ have a common characteristic of being low endotoxin alginic acids, their alginic acids differ in terms of molecular weight, and this difference is thought to lead to differences in cartilage regenerative effects. Although viscosity can be adjusted by the concentration of alginic acid, in an experiment in which different concentrations of alginic acid gels (0.5 to 4%) were embedded with chondrocytes, transplanted beneath the skin of mice and confirmed for the generation of cartilage, the concentration of alginic acid was reported to not have an effect on cartilage generation effects (Keith T. Paige et al., "De Novo Cartilage Generation Using Calcium Alginate-Chondrocyte Constructs", Plastic and Reconstructive Surgery, Vol. 97: 1996, p. 168-178).

Thus, the difference in cartilage regenerative effects between Sea Matrix™ and Pronova™ is thought to be attributable to molecular weight. Namely, although the use of low endotoxin alginic acid allows the obtaining of a composition having high bioaffinity with low levels of degeneration and inflammatory responses in surrounding cartilage, by also using alginic acid having a high molecular weight, it was found that a composition for regenerating cartilage or therapeutic composition can be obtained that has extremely superior cartilage regenerative effects allowing regeneration of cartilage even without embedding cells therein. Low endotoxin alginic acid having a weight average molecular weight of at least 500,000 or more, and preferably 650,000 or more, is useful for cartilage regeneration, and that having a weight average molecular weight of 1,000,000 to 2,000,000 was found to be more preferable, and that having a weight average molecular weight of about 1,500,000 to 2,000,000 was found to be particularly preferable.

Example 3

Rabbit Osteoarthritis Model (Anterior Cruciate Ligament (ACL) Resection Model)

(1) Method

An OA model was created in both knee joints of female Japanese white rabbits (body weights: 2.6 to 2.9 kg) in accordance with the method of Vignon, E. et al. (Vignon, E., Bejui, J., Mathieu, P., Hartmann, J D, Ville, G., Evreux, J C, et al., Histological cartilage changes in a rabbit model of osteoarthritis, J. Rheumatol., 1987:14 (Spec No): 104-6). Three animals each (6 knees) were assigned to the following four groups.

A) Control group (physiological saline)
B) 1% sodium hyaluronate solution dose group (molecular weight: approx. 900,000, viscosity: approx. 2300 mPa·s)
C) 1% purified sodium alginate solution dose group (molecular weight: approx. 1,700,000, viscosity: approx. 500 mPa·s)
D) 2% purified sodium alginate solution dose group (molecular weight: approx. 1,700,000, viscosity: approx. 5000 mPa·s)

The solutions of B) to D) were prepared using physiological saline. The purified sodium alginate of C) and D) were the same as the purified sodium alginate used in Example 1 (Kimica Corp., Mochida International Ltd., Sea Matrix (sterilized), Serial No. B5Y01).

Following resection of the anterior cruciate ligament, each of the solutions A) to D) above were administered into the articular cavity in weeks 4, 5, 6, 7 and 8 (total of 5 administrations given once per week).

The solutions were administered using a 27G needle by penetrating the patellar tendon and injecting 0.3 mL/knee per administration. The rabbits were sacrificed in week 9 to acquire knee joint tissue specimens. Inflammation from infections, foreign body reactions and the like were not observed in any of the knees.

Figure 9:
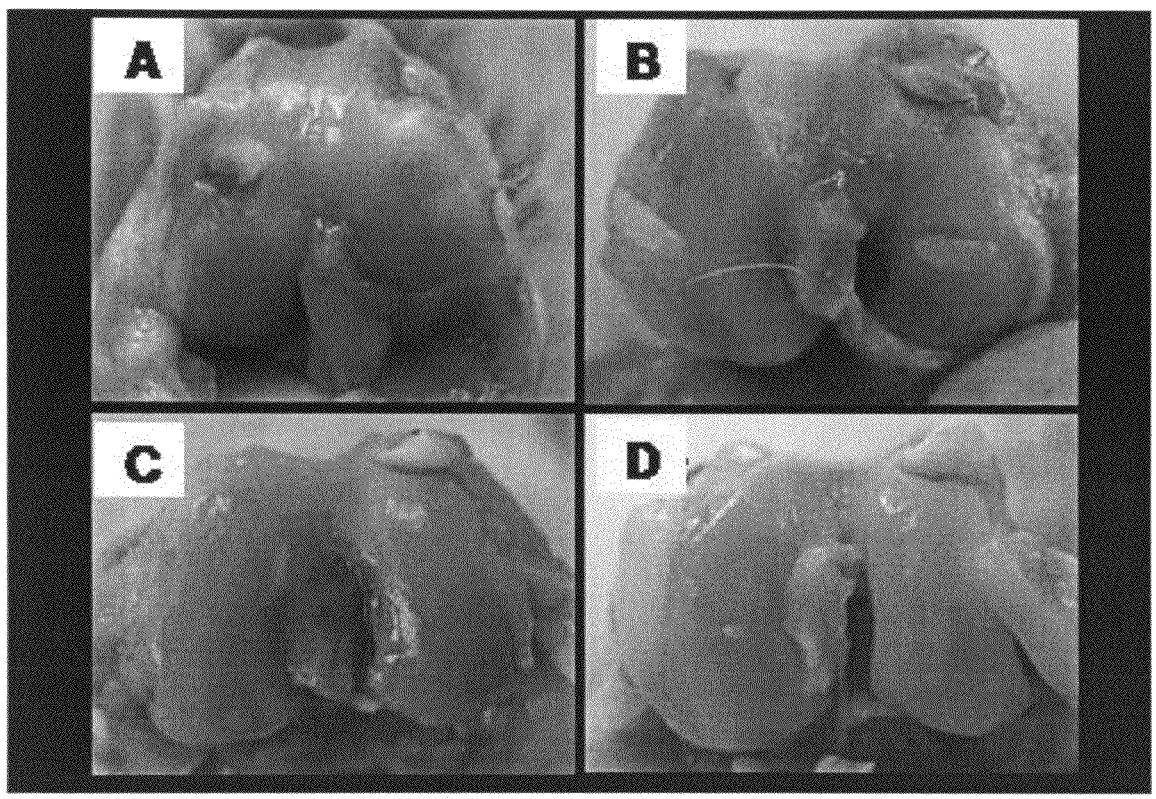
FIG. 9A-D show photographs of the appearance of knee joints in a rabbit osteoarthritis model of Example 3.

(2) Results
(General Observations)
The appearance of the entire knee joint (knee articular cartilage of the femur and tibia) was observed macroscopically. Those results are shown in FIG. 9. In group A (physiological saline dose group), numerous findings of osteoarthritis, including cartilage defects and osteophytes, were observed macroscopically. The degree of cartilage injury (size, depth) was milder in the other groups than in group A. Scoring of the macroscopic findings yielded similar results.

(Staining)

Figure 10:
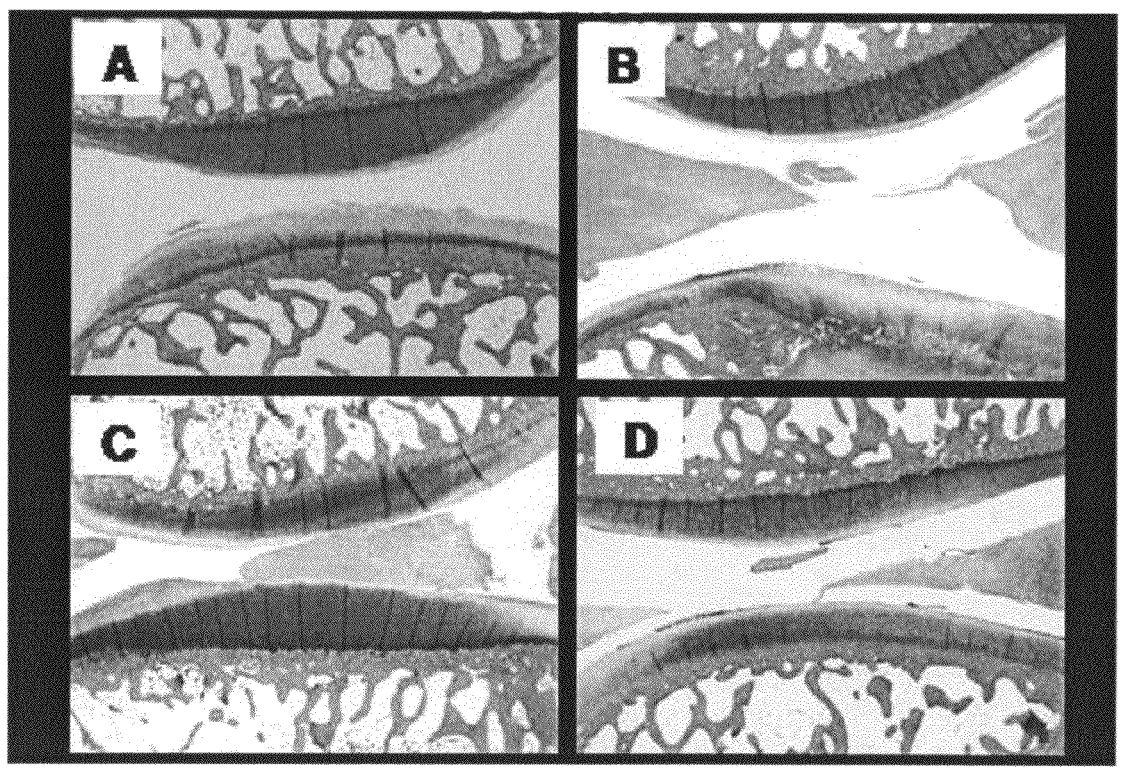
FIG. 10A-D show photographs of tissue staining of knee joint tissue in a rabbit osteoarthritis model of Example 3.

The knee joint tissue specimens were fixed with paraformaldehyde, decalcified and embedded in paraffin. The specimens were evaluated histologically by safranin-O staining. Those results are shown in FIG. 10. The upper portions of each figure indicate femoral cartilage, while the lower portions indicate tibial cartilage, and cartilage degenerative changes were assessed in cartilage at both locations. Decreased staining of cartilage matrix and increased coarseness of cartilage surface were observed in group A (physiological saline dose group). In group B (1% sodium hyaluronate solution dose group), although cartilage surface was smoother than in group A, decreased staining was observed. In group C (1% purified sodium alginate solution dose group) and group D (2% purified sodium alginate solution dose group), cartilage surface was smooth and decreases in staining were mild as compared with groups A and B. In addition, residual alginic acid was present on the cartilage surface.

On the basis of the above findings, intra-articular injection of sodium alginate demonstrated action that inhibited cartilage degeneration and protected cartilage in an ACL resection OA model, and effects were observed that were equal to or better than administration of 1% sodium hyaluronate solution used as a therapeutic drug for osteoarthritis. In addition, since sodium alginate was adhered to the cartilage surface, sodium alginate was confirmed to demonstrate affinity with articular cartilage as well as cover and protect cartilage surfaces.

Example 4

Evaluation of Therapeutic Effects of Alginic Acid of Different Molecular Weights in a Rabbit Osteoarthritis Model (Anterior Cruciate Ligament (ACL) Resection Model)

(1) Method

An OA model was created in both knee joints of female Japanese white rabbits (body weights: 2.6 to 2.9 kg) in accordance with the method of Vignon, E. et al. (Vignon, E., Bejui, J., Mathieu, P., Hartmann, J D, Ville, G., Evreux, J C, et al., Histological cartilage changes in a rabbit model of osteoarthritis, J. Rheumatol., 1987:14 (Spec No): 104-6). Five animals each (10 knees) were assigned to the following five groups.

A) Control group (physiological saline)

B) 1% sodium hyaluronate solution dose group (ARTZ (registered trademark), Kaken Pharmaceutical Co., Ltd., molecular weight: approx. 900,000, viscosity: approx. 2300 mPa·s)

C) 2% purified sodium alginate solution dose group (Pronova™ SLM$_{20}$, FMC Biopolymer Inc., molecular weight: approx. 400,000)

D) 2% purified sodium alginate solution dose group (Kimica Corp., sterilized, molecular weight: approx. 1,000,000)

E) 2% purified sodium alginate solution dose group (Sea Matrix (sterilized), Kimica Corp., molecular weight: approx. 1,700,000)

The solutions of C) to E) were prepared using physiological saline.

Following resection of the anterior cruciate ligament, each of the solutions A) to E) above were administered into the articular cavity in weeks 4, 5, 6, 7 and 8 (total of 5 administrations given once per week). The solutions were administered using a 27G needle by penetrating the patellar tendon and injecting 0.3 mL/knee per administration. The rabbits were sacrificed in week 9 to acquire knee joint tissue specimens. Inflammation from infections, foreign body reactions and the like were not observed in any of the knees.

(2) Results (General Observations)

Figure 11:
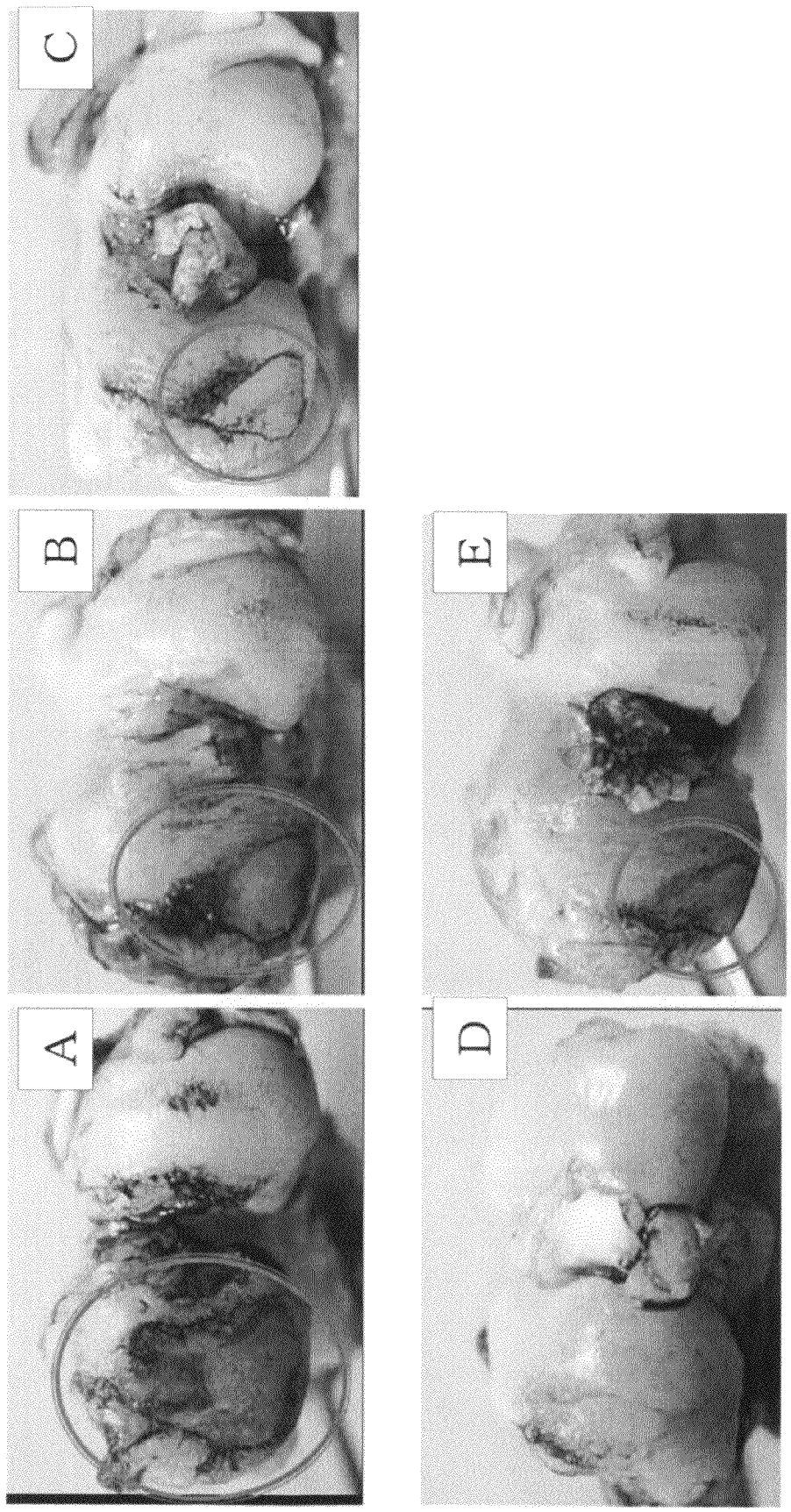
FIG. 11A-E show photographs of the appearance of knee joints in a rabbit osteoarthritis model of Example 4 after staining with India ink. In the photographs, the encircled areas indicate boundaries between cartilage injury lesions stained with India ink and normal cartilage. A) Control group; B) 1% sodium hyaluronate dose group; C) 2% sodium alginate dose group (molecular weight: 400,000); D) 2% sodium alginate dose group (molecular weight: 1,000,000); E) 2% sodium alginate dose group (molecular weight: 1,700,000). Furthermore, the photographs show examples of multiple specimens.
Figure 12:
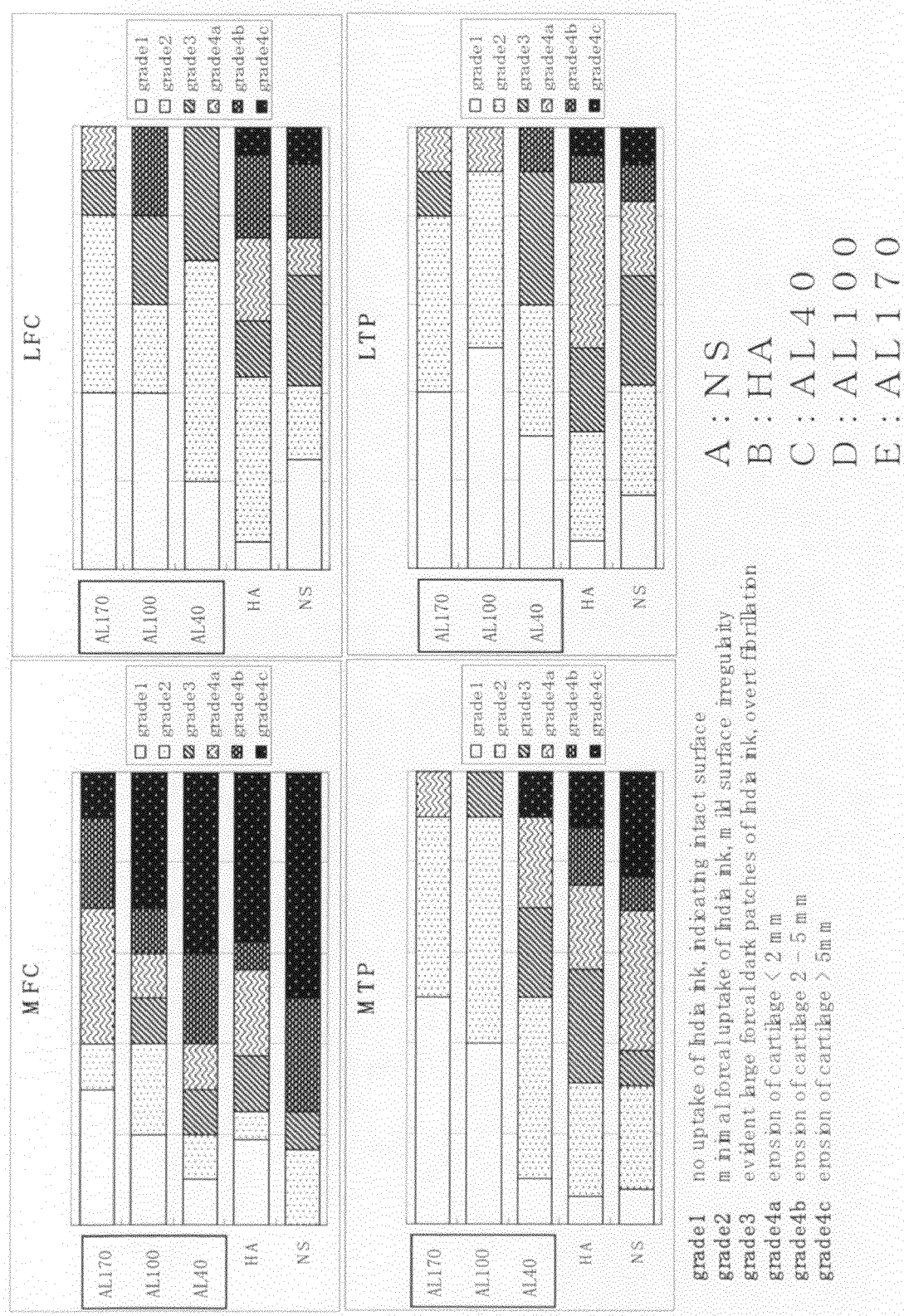
FIG. 12 shows the results of scoring macroscopic findings of knee joints stained with India ink in a rabbit osteoarthritis model of Example 4. NS, HA, AL40, AL100 and AL170 respectively correspond to A) to E) (same as FIG. 11). Grade 1 indicates an uninjured surface not stained with India ink (no uptake of India ink, indicating intact surface). Grade 2 indicates focal staining with India ink and mild injury to the surface (minimal focal uptake of India ink, mild surface irregularity). Grade 3 indicates large, well-defined staining with India ink and obvious fibrillation (evident large focal dark patches of India ink, overt fibrillation). Grade 4a indicates cartilage erosion of less than 2 mm (erosion of cartilage<2 mm). Grade 4b indicates cartilage erosion of 2 to 5 mm (erosion of cartilage 2-5 mm). Grade 4c indicates cartilage erosion of greater than 5 mm (erosion of cartilage>5 mm).

The appearance of the entire knee joint (knee articular cartilage of the femur and tibia) was observed macroscopically. In order to evaluate the degree of injury to the cartilage surface, the specimens were stained in India ink in accordance with the method of Choji Shimizu et al. and then scored (J. Rheumatol., Vol. 25, pp. 1813-1819, 1998). Macroscopic findings are shown in FIG. 11. When staining with India ink, boundaries between cartilage injury lesions and normal cartilage are colored. In group A (physiological saline dose group), numerous findings of osteoarthritis, including deep and wide-ranging cartilage defects and osteophytes, were observed macroscopically. The degree of cartilage injury (size, depth) was milder in the other groups than in group A. The results of scoring the macroscopic findings are shown in FIG. 12. The knee joints were observed at four locations consisting of the Medial Femoral Condyle (MFC), Medial Tibial Plateau (MTP), Lateral Femoral Condyle (LFC) and Lateral Tibial Plateau (LTP). The degree of cartilage injury was milder in groups B to E than in group A at all of these sites. In addition, the degree of cartilage injury tended to be milder in groups D and E than in groups B and C. Differences in cartilage degenerative change inhibitory effects, cartilage protective effects and cartilage repair effects were thought to be present due to differences in molecular weight of alginic acid.

(Proteoglycan Staining)

Figure 13:
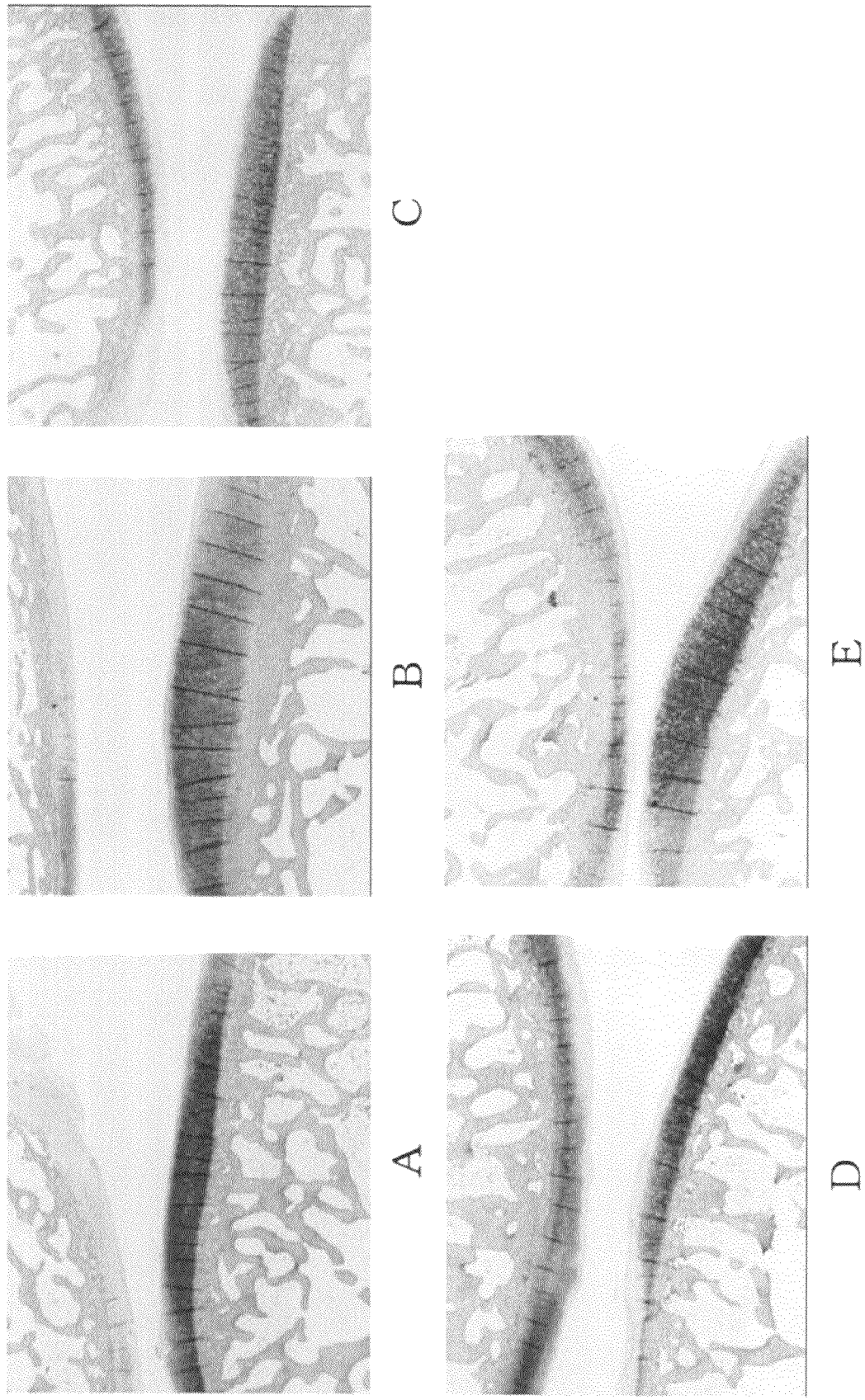
FIG. 13A-E show photographs of staining of knee joint tissue with Safranin-O in a rabbit osteoarthritis model of Example 4. A) to E) are the same as in FIG. 11. Furthermore, the photographs show examples of multiple specimens.

The knee joint tissue specimens were fixed in paraformaldehyde, decalcified and embedded in paraffin. The specimens were evaluated histologically by safranin-O staining. Those results are shown in FIG. 13. The upper portions of each figure indicate femoral cartilage, while the lower portions indicate tibial cartilage, and cartilage degenerative changes were assessed in cartilage at both locations. Decreased staining of cartilage matrix and increased coarseness of cartilage surface were observed in group A (physiological saline dose group). In group B (1% sodium hyaluronate solution dose group), although cartilage surface was smoother than in group A, decreased staining was observed. In the sodium alginate solution dose groups (groups C to E), cartilage surface was smooth and decreases in staining were mild as compared with groups A and B. In addition, residual alginic acid was present on the cartilage surface.

(Overall Histopathological Evaluation)

Macroscopic observations and observations by staining were comprehensively evaluated by scoring in accordance with the method of Toshiyuki Kikuchi et al. to evaluate effects of the administered drugs (Osteoarthritis and Cartilage, Vol. 4, pp. 99-110, 1996). Medial femoral condyle were evaluated to one of four levels for the 8 parameters indicated below, and the total score was used as an osteoarthritis lesion score.

(1) Loss of cartilage surface, (2) cartilage erosion, (3) fibrosis and cracking, (4) loss of stainable proteoglycan, (5) disturbances in chondrocyte arrangement, (6) loss of chondrocytes, (7) loss of subchondral bone, and (8) formation of chondrocyte clusters.

Figure 14:
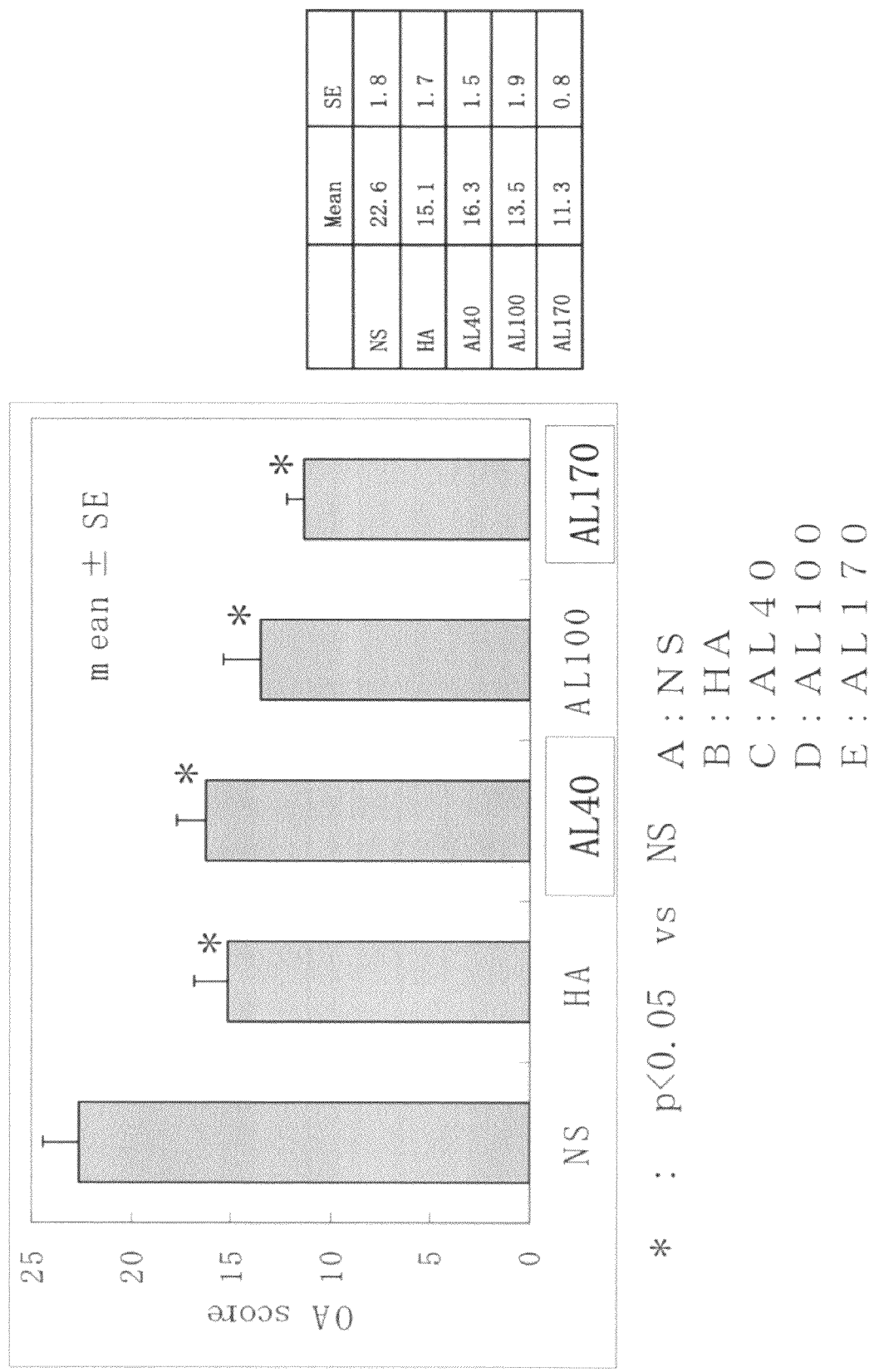
FIG. 14 shows the results of scoring general histopathological evaluations in a rabbit osteoarthritis model of Example 4. NS, HA, AL40, AL100 and AL170 respectively correspond to A) to E) (same as FIG. 11).

ANOVA was used to test for the presence of a significant difference between groups, and subsequent comparisons between each group were made at a level of significance of p<0.05 using a post hoc test. The results are shown in FIG. 14. Osteoarthritis lesion scores were significantly lower in groups B to E versus group A. In addition, although superior effects were observed in the high molecular weight alginic acid dose groups (groups D and E) as compared with the hyaluronic acid dose group (group B), effects of the low molecular weight alginic acid dose group (group C) were about the same as those of the hyaluronic acid dose group.

On the basis of the above findings, intra-articular injection of sodium alginate demonstrated action that inhibited cartilage degenerative changes and protected cartilage in an ACL resection OA model, and effects were observed that were equal to or better than administration of 1% sodium hyaluronate solution used as a therapeutic drug for osteoarthritis. In particular, high molecular weight alginic acid demonstrated superior therapeutic effects to hyaluronic acid. Furthermore, although the three types of alginic acid differed in terms of viscosity, since alginic acid having viscosity lower than that of hyaluronic acid is observed to demonstrate effects equal to or greater than those of hyaluronic acid, differences in therapeutic effects are thought to be attributable to differences in the substance used and molecular weight rather than differences in viscosity.

In the ACL resection OA model used in this experiment, the drugs were administered starting 4 weeks after ACL resection. Thus, decreases in osteoarthritis lesion scores observed in the drug dose groups are thought to be the combined result of effects inhibiting the progression of lesions due to inhibition of cartilage degenerative changes and protection of cartilage, as well as cartilage repair action on cartilage injuries that had already occurred. According to the paper by the above-mentioned Toshiyuki Kikuchi cited as a reference in this experiment, OA scores are reported to reach 20 to 25 in physiological saline dose groups. Since drug administration was started in week 4 after ACL resection in this experiment, there is the possibility that OA scores decreased as a result of improvement of cartilage status due to the effects of the drugs as a result of starting administration from a state in which OA scores were about 20 to 25. In addition, since the score for normal joints is 8 in the evaluation system used in this experiment, the mean OA score (11.3) in group E (alginic acid having a molecular weight of 1,700,000) can be said to approach the score for normal joints and be an extremely good score.

Example 5

Study of Method of Measuring Molecular Weight of Alginic Acid

Different values are known to be obtained when measuring the molecular weight of high molecular weight substances derived from a natural origin depending on the measurement method. According to ASTM F2064-00 (ASTM International Publication (2006); the American Society for Testing and Materials is an organization engaged in the international standardization and establishment of specifications of industrial material standards and testing method standards), the use of SEC-MALLS (Size Exclusion Chromatography with Multiple Angle Laser Light Scattering Detection) is recommended for measurement of molecular weight. Therefore, a comparison was made between measurement of the molecular weight of the sodium alginate used in Example 4 by SEC-MALLS and by gel filtration chromatography as described in Example 2. Furthermore, SEC-MALLS combines the use of a multiple angle laser light scattering detector (MALLS) with gel filtration chromatography.

(1) Method

Measurement by gel filtration chromatography was carried out in the same manner as Example 2. Measurement by SEC-MALLS was carried out under the conditions indicated below.

Multiple angle laser light scattering detector: DAWN HELEOS, Wyatt Technology

Column: Shodex SB-806M, 2 columns (Showa Denko K.K.)

Eluate: 200 mM Aqueous sodium nitrate solution

Flow rate: 1.0 mL/min (2) Results

TABLE 2

|  | AL170 | AL100 | AL40 |
| --- | --- | --- | --- |
| Weight average molecular weight as determined by gel filtration chromatography | 1,700,000 | 1,000,000 | 410,000 |
| Weight average molecular weight as determined by SEC-MALLS | 185,000 | 149,000 | 128,000 |
| (Reference) Pharmacological effects in Example 4 | Very good | Very good | Good |

The same purified (low endotoxin) sodium alginate used in Example 4 is used for AL170, AL100 and AL40.

AL170: Kimica Corp., Mochida International Ltd., Sea Matrix (sterilized), 1% viscosity: approx. 500 mPa·s AL100: Kimica Corp., sterilized, 1% viscosity: approx. 100 mPa·s AL40: FMC Biopolymer Inc., Pronova™ $SLM_{20}$, 1% viscosity: approx. 30 mPa·s (3) Discussion As shown in Table 2, differences in the molecular weights of three types of alginates as determined by SEC-MALLS were only observed within a range that did not definitively indicate a difference between them, and those values differed considerably from measurement results obtained by gel filtration chromatography. As shown in Example 4, since there were well-defined differences in pharmacological effects between the samples used, molecular weights determined by gel filtration chromatography were found to demonstrate a higher correlation with therapeutic effects of alginates than molecular weights as determined by SEC-MALLS, and molecular weights determined by gel filtration chromatography were found to be suitable as parameters for specifying a preferable molecular weight range of alginates used in the composition for treating a joint disease.

Example 6

Effects of Alginic Acid on Experimental Arthritis Pain in Rats (1) Method

Rats with arthritis induced by intra-articular injection of needle-shaped monosodium urate (MSU) crystals present with an abnormal gait due to pain. A experimental arthritis pain model in rats administered MSU was prepared in accordance with the method of Shizuhiko Ihara, et al. (Folia Pharmacol. Japon, Vol. 100, pp. 359-365 (1992)) to assess the effects of intra-articular administration of sodium alginate.

Male Crl:CD rats were purchased at age 5 weeks and used in the experiment following a one week acclimation period.

0.05 mL of a 5.0% physiological saline suspension of MSU were injected into the right knee joint of the rats under anesthesia followed by observation of gait at 2, 4, 6 and 24 hours after injection. Gait was evaluated by scoring to one of five grades consisting of normal gait (0 points), mild limping (1 point), moderate limping (2 points), walking on toes (3 points) and walking on three legs (4 points). Ten animals were assigned to each of the five groups indicated below.

A) Control group (physiological saline dose group)

B) 1% sodium hyaluronate solution dose group (ARTZ (registered trademark), Kaken Pharmaceutical Co., Ltd., molecular weight:
approx. 900,000)

C) 2% purified sodium alginate solution dose group (Kimica Corp., sterilized, molecular weight: approx. 1,000,000)

D) 1% purified sodium alginate solution dose group (Sea Matrix (sterilized), Kimica Corp., molecular weight: approx. 1,700,000)

E) 2% purified sodium alginate solution dose group (Sea Matrix (sterilized), Kimica Corp., molecular weight: approx. 1,700,000) 50 μL of each solution were administered to the same site of the joint one hour prior to injection of MSU.

(2) Results and Discussion

Figure 15:
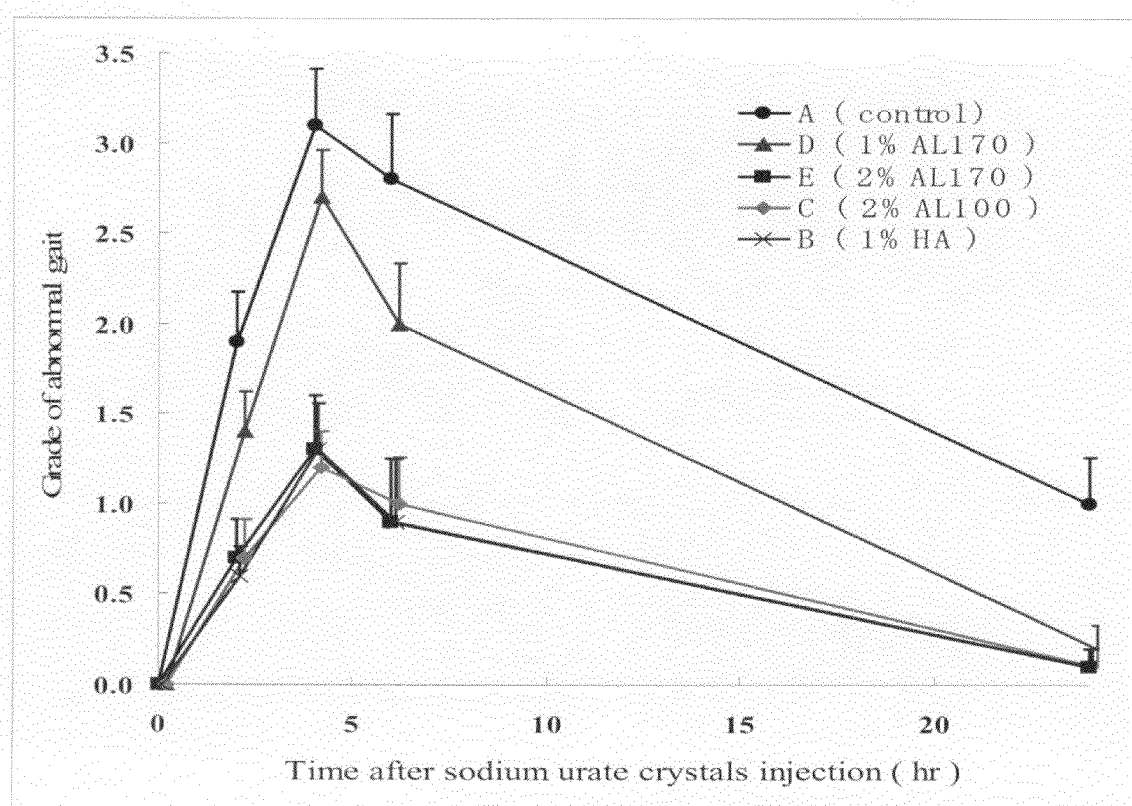
FIG. 15 shows time-based changes in gait scores in a rat experimental arthritis pain model of Example 6. A) Control group (NS); B) 1% sodium hyaluronate dose group (1% HA); C) 2% sodium alginate dose group (molecular weight: 1,000,000) (2% AL100); D) 1% sodium alginate dose group (molecular weight: 1,700,000) (1% AL170); E) 2% sodium alginate dose group (molecular weight: 1,700,000) (2% AL170). *: $p<0.05$ vs. NS.

Time-based changes in gait scores are shown in FIG. 15. The gait scores of the 1% sodium hyaluronate solution dose group (group B) and 2% sodium alginate solution dose groups (groups C and E) were significant lower than the control group (group A), and pain suppressive effects were observed. Dose-dependent pain suppressive effects were observed in a comparison of the 1% and 2% solutions containing sodium alginate having a molecular weight of about 1,700,00 (groups D and E). In addition, the 2% sodium alginate solutions having molecular weights of 1,000,000 and 1,700,000 demonstrated equal pain suppressive effects despite having different viscosities of about 300 mPa·s and about 5000 mPa·s, respectively.

In joints, MSU acts directly or indirectly on synovial cells and neutrophils, and is thought to cause arthritis through the production of cytokines and the like (above-mentioned publication by Shizuhiko Ihara, et al.). Namely, MSU induces pain as a result of inflammatory reaction being induced thereby. Sodium alginate solution demonstrated pain suppressive effects in this model, and effects observed were equal to those of sodium hyaluronate, which is used as a therapeutic drug for osteoarthritis and as a joint pain suppressive drug for chronic rheumatoid arthritis. A monovalent metal salt of alginic acid was confirmed to have effects that inhibit inflammation and pain, and is believed to be useful as a therapeutic drug for osteroarthritis, frozen shoulder and the like, while also being able to be applied to joint pain associated with rheumatoid arthritis.

In addition, sodium alginate having a molecular weight of 430,000 (Kimica Corp., sterilized) was observed to tend to have weaker pain suppressing effects than sodium alginate having a molecular weight of 1,000,000. This difference in pain suppressing effects was thought to be attributable to the difference in molecular weight of the alginic acid.

Example 7

Effects of Intra-articular Administration of Alginic Acid in Rabbit Rotator Cuff Rupture Model (1) Production of Rotator Cuff Rupture Model A rotator cuff rupture model was produced using Japanese white rabbits. After shaving both shoulder joints of the animals under general anesthesia using ketamine hydrochloride, the shoulder joints were exposed with a posterior approach using a sterile procedure. The omovertebral muscle was then separated to produce defects measuring 10×7 mm in the infraspinatus muscle tendon and the insertion thereof on the side of the humeral head. 0.3 mL of a 2% purified sodium alginate solution (Sea Matrix (sterilized), Kimica Corp., molecular weight: approx. 1,700,000) were injected into the right shoulder joint. 0.3 mL of physiological saline (Otsuka Pharmaceutical Co., Ltd.) were injected into the left shoulder joint using the same procedure for use as a control. Following the procedure, the animals were allowed to move freely in their cages without immobilizing the upper limbs. Following the procedure, after continuously administering alginate solution into the right shoulder and physiological saline into the left shoulder once a week for five weeks (total of 5 administrations), the animals were sacrificed by large-dose intravenous administration of pentobarbital followed by acquisition of shoulder joint tissue specimens.

(2) Results

Figure 16:
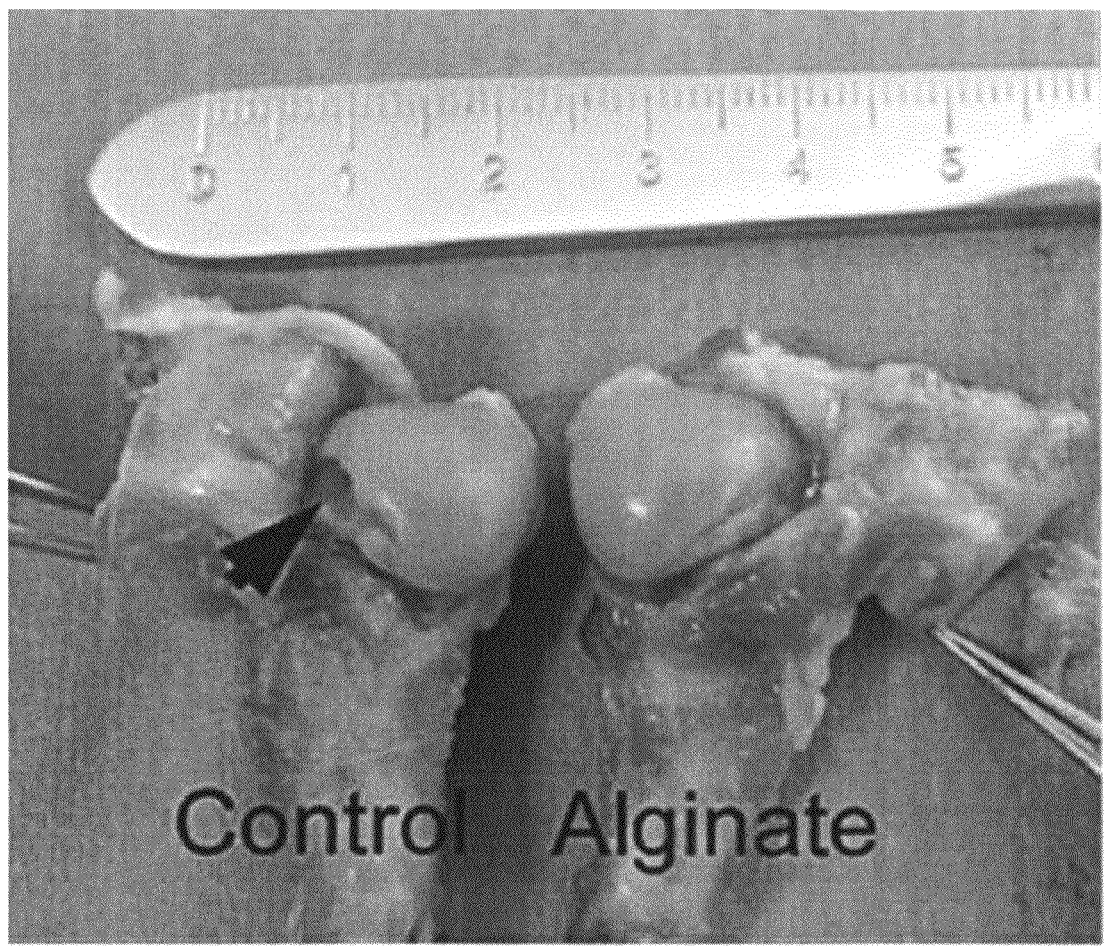
FIG. 16 shows a photograph of humeral heads in a rabbit rotator cuff rupture model of Example 7. The black arrow indicates a cartilage injury lesions. "Control" indicates a physiological saline dose group, while "Alginate" indicates an alginic acid dose group.

Although severe cartilage defects were observed at sites along the rotator cuff tear in the control group following macroscopic observation of the humeral head, there were no well-defined cartilage injuries observed in the alginate dose group (FIG. 16). Sodium alginate demonstrated cartilage protective effects and inhibited the occurrence and progress of cartilage injury.

Example 8

Measurement of Knee Joint Friction Coefficients in a Rabbit Osteoarthritis Model (Anterior Cruciate Ligament (ACL) Detachment Model)

(1) Method

A rabbit OA model was created in the same manner as Example 4, OA knee joint specimens (n=4), administered with 1% sodium hyaluronate solution (ARTZ (registered trademark), Kaken Pharmaceutical Co., Ltd., molecular weight: approx. 900,000, viscosity: approx. 2300 mPa·s) and OA knee joint specimens (n=4) administered with 2% purified sodium alginate solution (Kimica Corp., sterilized, molecular weight: approx. 1,000,000) were acquired, and knee joint friction coefficients were measured in accordance with the method of Tanaka, E. et al. (J. Dent. Res., 2004 May; 83(5): 404-7). Administration of each drug was carried out in the same manner as Example 4, and the rabbits were sacrificed in week 9 following anterior cruciate ligament excision to acquire knee joint specimens. Measurements were carried out by bending the knee at an angle of 30 degrees while applying a load of 1.8 kg for a measuring time of 120 seconds, and measurements were carried out five times on each specimen. A normal knee joint (n=1) was used as a control.

(2) Results

Figure 17:
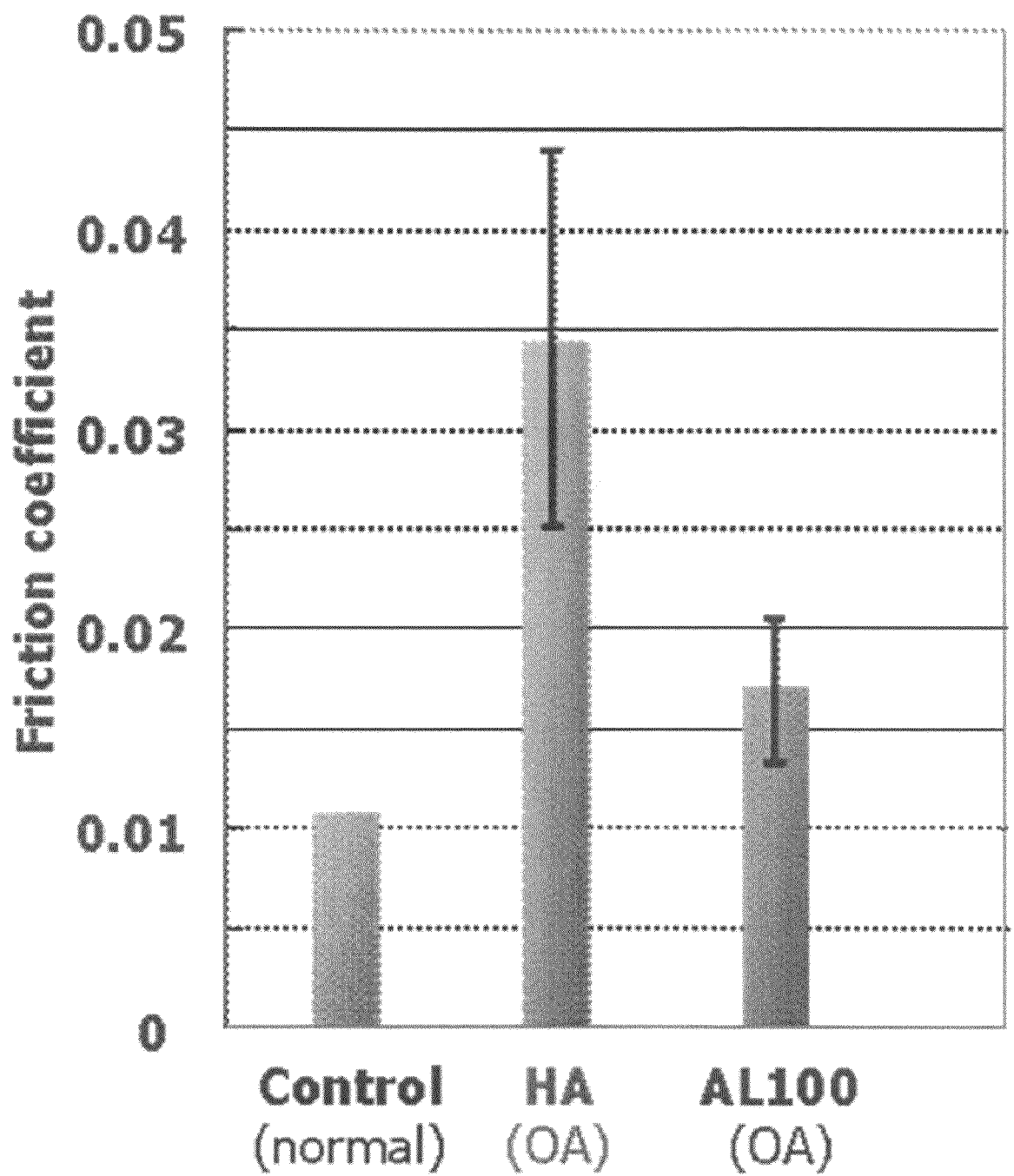
FIG. 17 is a graph showing friction coefficients of knee joint specimens of a rabbit osteoarthritis model of Example 8. Friction coefficients are plotted on the vertical axis. "Control (normal)" indicates a normal joint, "HA(OA)" indicates an OA joint administered hyaluronic acid, and "AL100(OA)" indicates an OA joint administered alginic acid.

The OA knee joints administered alginic acid demonstrated significantly lower friction coefficients than the OA knee joint specimens administered hyaluronic acid (FIG. 17). Although normal knee joints inherently demonstrate low values for friction coefficient, as the pathology of OA progresses, the friction coefficient increases and this increase further promotes destruction of tissue. The reason for the low friction coefficients in the OA knee joint specimens administered alginic acid is thought to be due to OA symptoms being mild, and reflected the tissue being maintained in a favorable state. Namely, the tissue status observed in the macroscopic findings and histological evaluations of Example 4 are thought to have been reflected in knee joint friction coefficients.

Example 9

Effects of Intra-Articular Administration of Alginic Acid for Collagen-Induced Arthritis in Rats A collagen-induced arthritis (CIA) model is frequently used as a model of rheumatoid arthritis since the pathology resembles that of human rheumatoid arthritis (RA). A collagen-induced arthritis model was created in rats in order to examine the effects of intra-articular administration of sodium alginate.

(1) Creation of Animal Model

Ten-week-old DA/Slc (SPF) male rats were purchased and used in the experiment after a one-week acclimation period. An emulsion was prepared by dissolving bovine type II collagen (Collagen Technology Research Association) in 0.01 mol/L aqueous acetic acid solution to a concentration of 1.5 mg/mL and using an equal volume of Freund's incomplete adjuvant (Difco). A total of 0.4 mL (collagen content: 300 μg) of this emulsion was administered (sensitized) into the skin on the back of the rats (at 4 to 6 locations) to induce arthritis.

(2) Administration of Test Substances

Ten animals each were assigned to the five groups indicated below.

A) Control group (physiological saline dose group)

B) 1% aqueous sodium hyaluronate dose group (ARTZ (registered trademark), Kaken Pharmaceutical Co., Ltd., molecular weight: approx. 900,000)

C) 2% aqueous purified sodium alginate dose group (Kimica Corp., sterilized, molecular weight: approx. 1,000,000)

D) 1% aqueous purified sodium alginate dose group (Sea Matrix (sterilized), Kimica Corp., molecular weight: approx. 1,700,000)

E) 2% aqueous purified sodium alginate dose group (Sea Matrix (sterilized), Kimica Corp., molecular weight: approx. 1,700,000)

The dose volume of each administered substance was 0.05 mL/rat, and the substances were administered into the articular cavity of the left hind knee joint of the animals using a 1 mL syringe and 26 G injection needle. The animals were dosed once a day on five days consisting of days 0 (day of collagen administration), 5, 10, 15 and 20 following sensitization.

(3) Macroscopic Observation of Joint Inflammation

The left hind legs of the animals were macroscopically observed daily after sensitization and the presence and degree of arthritis were evaluated by scoring according to the criteria indicated below.

Figure 18:
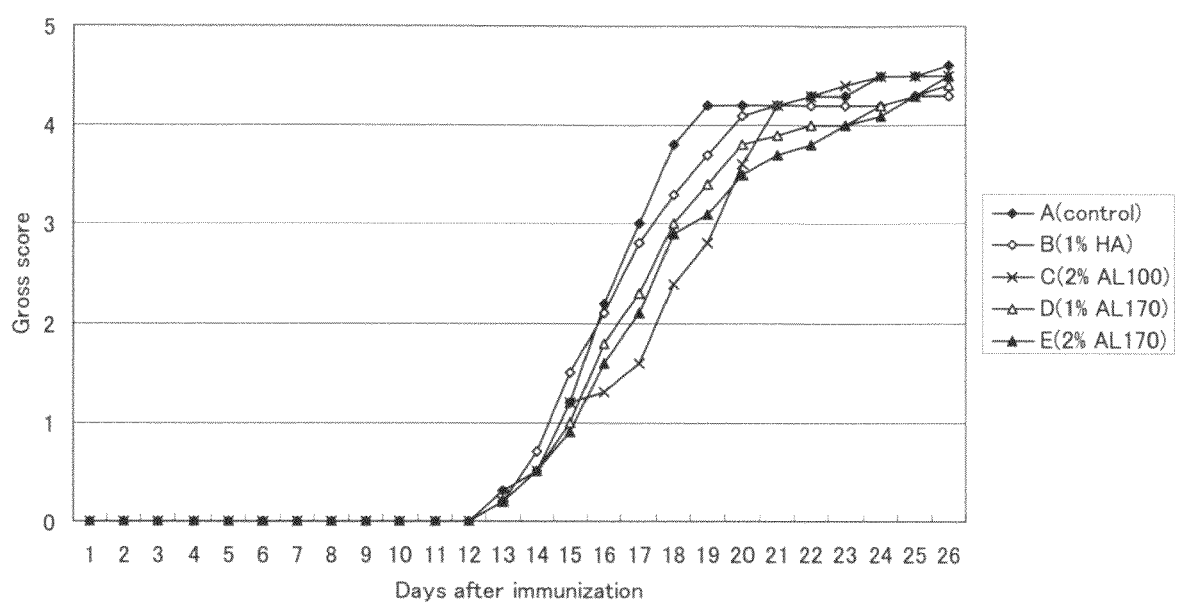
FIG. 18 is a graph showing time-based changes in the degree of arthritis following antigen sensitization in a rat collagen-induced arthritis model of Example 9. Arthritis scores are plotted on the vertical axis, while the number of days after antigen sensitization is plotted on the horizontal axis. A) indicates a control group, B) a 1% sodium hyaluronate dose group, C) a 2% sodium alginate dose group (molecular weight: 1,000,000), D) a 1% sodium alginate dose group (molecular weight: 1,700,000) and E) a 2% sodium alginate dose group (molecular weight: 1,700,000).

Score 0: Normal
  Score 1: Redness observed
  Score 2: Redness and slight edema observed in toes
  Score 3: Edema extending from toes to full length of paw
  Score 4: Severe edema observed
  Score 5: Joint deformation observed The results are shown in FIG. 18. Rapid onset of arthritis was observed starting on day 14 after sensitization in the control group, and degree of arthritis increased through day 25. Although similar degrees of onset were observed in all groups by day 25 after sensitization, onset tended to be delayed in the hyaluronic acid dose group (group B) and aqueous sodium alginate dose groups (groups C, D and E) as compared with the control group. The degree of the delay was observed more strongly in the aqueous sodium alginate dose groups (groups C, D and E) than in the hyaluronic acid dose group (group B). The test substance was therefore considered to have the potential to inhibit inflammation in joints.

(4) Histopathological Evaluations

Figure 19:
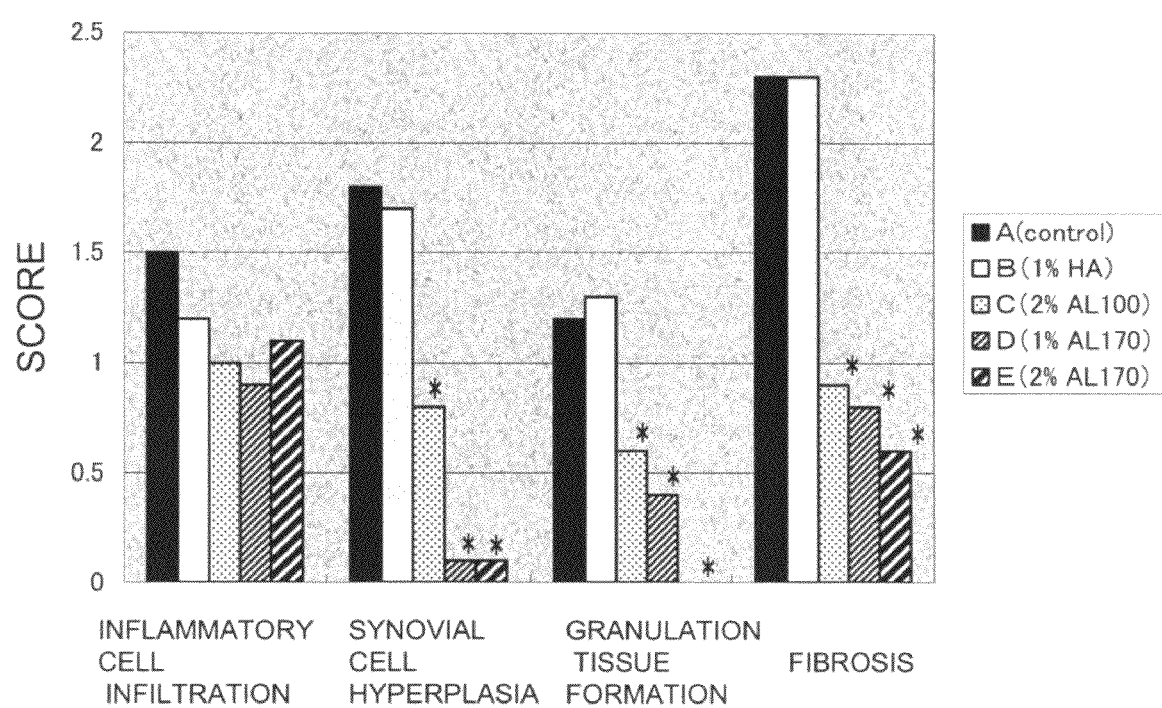
FIG. 19 shows the results of scoring histological evaluations of knee joint synovial tissue in a rat collagen-induced arthritis model of Example 9. A through E represent the same groups as in FIG. 18. *: $p<0.05$ vs. control
Figure 20:
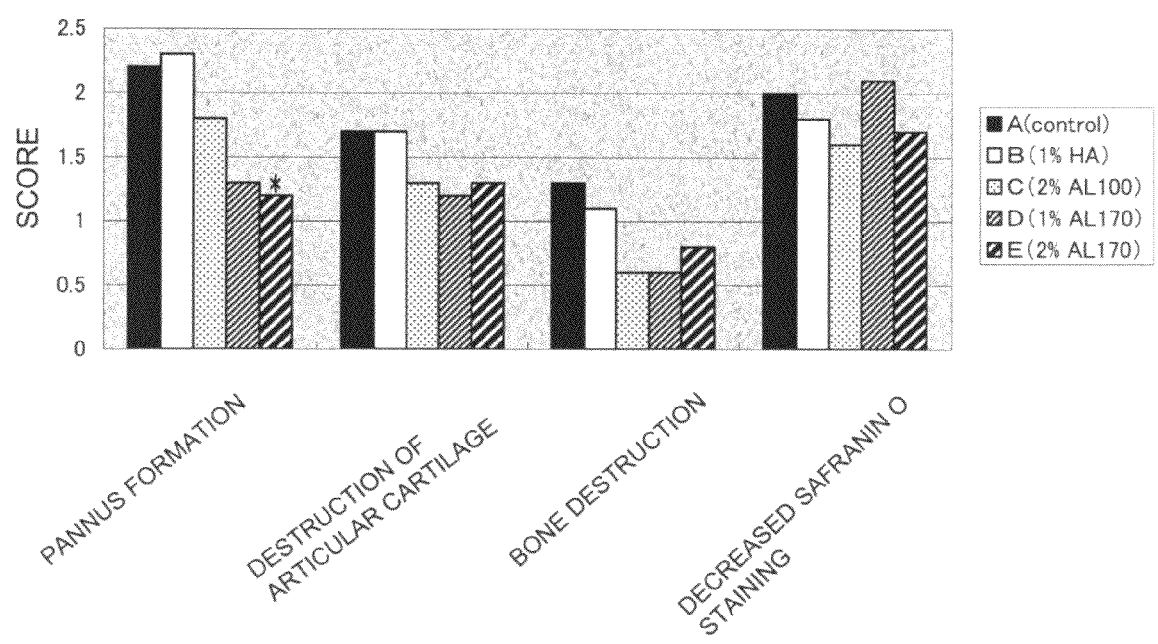
FIG. 20 shows the results of scoring histological evaluations of knee joint patella in a rat collagen-induced arthritis model of FIG. 9. A through E represent the same groups as in FIG. 18. *: $p<0.05$ vs. control
Figure 21:
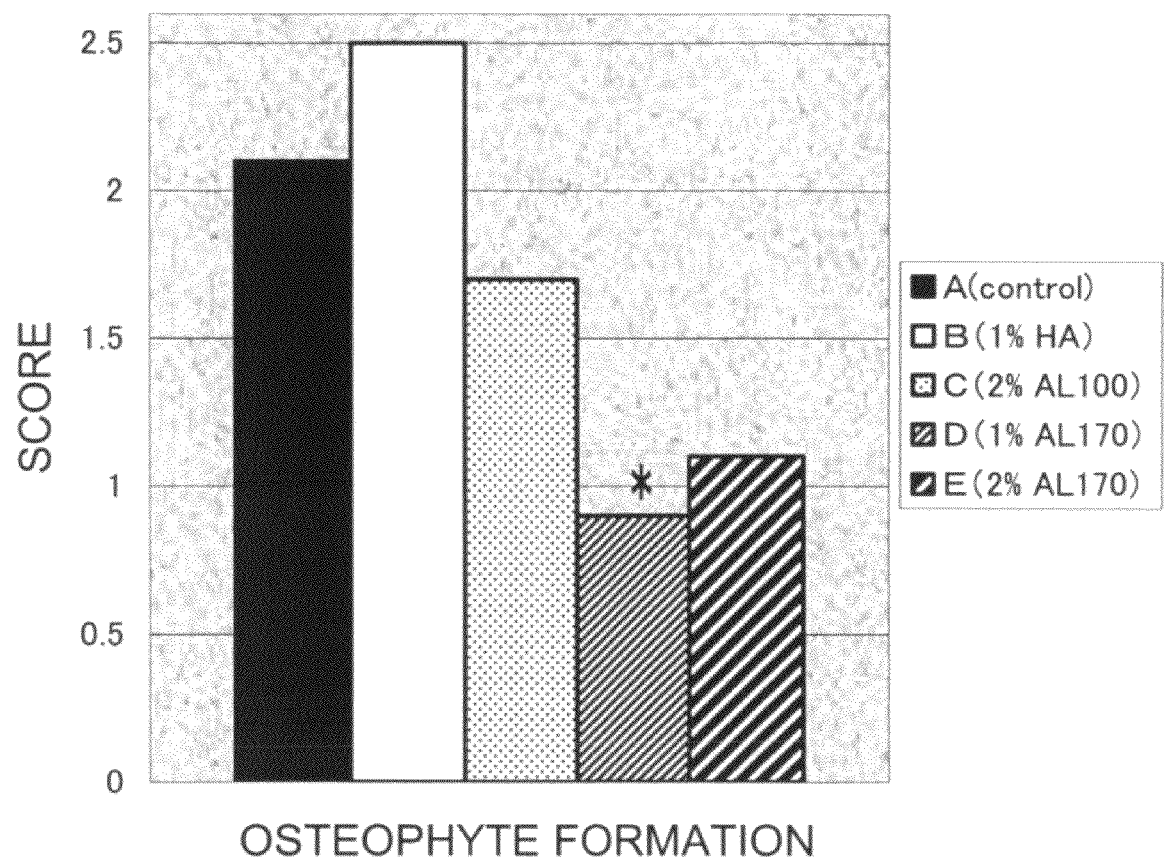
FIG. 21 shows the results of scoring histological evaluations of the lateral femoral condoyle of the knee joint in a rat collagen-induced arthritis model of Example 9. A through E represent the same groups as in FIG. 18. *: $p<0.05$ vs. control

The animals were sacrificed on day 25 after sensitization followed by excision of knee joint tissue from the left hind limb, fixing in formalin, decalcifying with aqueous 10% EDTA solution and fixing in paraffin. The specimens were stained with hematoxylin and eosin and with safranin O followed by histological evaluation. The specimens were evaluated by scoring to one of five levels consisting of no change (score: 0), slight change (score: 1), mild change (score: 2), intermediate change (score: 3) and severe change (score: 4) in accordance with evaluation parameters and evaluation criteria of collagen-induced arthritis. The synovial membrane was observed for infiltration of inflammatory cells, synovial cell hyperplasia, formation of granulation tissue and fibrosis, and the results of scoring those findings are shown in FIG. 19. The patella was observed for the formation of pannus on the surface of articular cartilage (including synovial hyperplasia), destruction of articular cartilage (including degeneration and fibrosis), bone destruction (resorption) and decreased safranin O staining (reduced proteoglycans), and the results of scoring those findings are shown in FIG. 20. Observation of osteophyte formation (reactive osteoid formation and periosteal new bone formation) was targeted at the lateral condoyle of the femur where it is easiest to form osteophytes. The results are shown in FIG. 21. The presence of a significant difference was tested with the Mann-Whitney U test.

In the synovial membrane, the aqueous sodium alginate dose groups (groups C, D and E) demonstrated significant synovial cell hyperplasia inhibitory effects, granulation tissue formation inhibitory effects and fibrosis inhibitory effects with respect to the control group. In addition, high molecular weight alginic acid demonstrated more potent effects.

In the patella, the aqueous sodium alginate dose groups (groups C, D and E) tended to inhibit pannus formation, articular cartilage destruction and bone destruction.

In the lateral condoyle of the femur, the aqueous sodium alginate dose groups (groups C, D and E) tended to inhibit osteophyte formation. In addition, high molecular weight alginic acid demonstrated more potent effects.

Inflammation and abnormal growth of the synovial membrane and an excessive immune response mediated by activated T-cells is said to be involved in the onset of rheumatoid arthritis, and destruction of joint tissue is said to progress as a result thereof. Aqueous sodium alginate solution strongly inhibited degeneration of synovial tissue by intra-articular administration to collagen-induced arthritis model animals. In addition, the aqueous alginate solution also demonstrated an inhibitory trend against destruction and degeneration of bone and cartilage. The aqueous sodium alginate solution was also observed to demonstrate tissue degeneration inhibitory effects superior to those of sodium hyaluronate solutions used for the treatment of joint pain in rheumatoid arthritis. Intra-articular injection of a solution of a salt of alginic acid is thought to allow the obtaining of therapeutic effects for rheumatoid arthritis in the form of inhibiting the progress of and improving tissue lesions.

INDUSTRIAL APPLICABILITY

The composition for treating a joint disease of the present invention has cartilage repair effects, effects that suppress cartilage degenerative changes, cartilage protective effects, effects that inhibit inflammation of joint tissue, effects that suppress pain caused by inflammation of joint tissue, effects that inhibit synovial tissue degeneration, and/or effects that inhibit osteochondral destruction by being injected into a joint in a liquid state, thereby enabling it to demonstrate therapeutic effects on a joint disease. The composition is particularly useful for the treatment of osteoarthritis, the treatment of frozen shoulder, alleviation of joint pain associated with rheumatoid arthritis, and treatment of rheumatoid arthritis.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What we claimed is:

1. A method of treating rheumatoid arthritis comprising: injecting into a joint of a subject in need thereof a composition containing a therapeutically effective amount of a low endotoxin monovalent metal salt of alginic acid, wherein the method does not comprise administering to the subject a curing agent of a monovalent metal salt of alginic acid.

2. The method of claim 1, wherein the composition does not contain cells.

3. The method of claim 1, wherein the low endotoxin monovalent metal salt of alginic acid has a weight average molecular weight of 500,000 or more as determined by gel filtration chromatography.

4. A method of inhibiting degeneration of synovial tissue in rheumatoid arthritis comprising: injecting into a joint of a subject in need thereof a composition containing a therapeutically effective amount of a low endotoxin monovalent metal salt of alginic acid, wherein the method does not comprise administering to the subject a curing agent of a monovalent metal salt of alginic acid.

5. The method of claim 4, wherein the composition does not contain cells.

6. The method of claim 4, wherein the low endotoxin monovalent metal salt of alginic acid has a weight average molecular weight of 500,000 or more as determined by gel filtration chromatography.

7. A method of inhibiting joint destruction in rheumatoid arthritis comprising: injecting into a joint of a subject in need thereof a composition containing a therapeutically effective amount of a low endotoxin monovalent metal salt of alginic acid, wherein the method does not comprise administering to the subject a curing agent of a monovalent metal salt of alginic acid.

8. The method of claim 7, wherein the composition does not contain cells.

9. The method of claim 7, wherein the low endotoxin monovalent metal salt of alginic acid has a weight average molecular weight of 500,000 or more as determined by gel filtration chromatography.

* * * * *